United States Patent [19]
Joenje et al.

[11] Patent Number: 5,952,190
[45] Date of Patent: Sep. 14, 1999

[54] CDNA FOR FANCONI ANEMIA COMPLEMENTATION GROUP A

[75] Inventors: Hans Joenje, Lelystad; Jerome R. Lo Ten Foe, An Almere, both of Netherlands

[73] Assignee: Fanconi Anemia Research Fund, Inc., Eugene, Oreg.

[21] Appl. No.: 08/726,012

[22] Filed: Oct. 4, 1996

[51] Int. Cl.$^6$ .............................. C12N 5/00; C12N 15/00; C07H 21/02; C07H 21/04

[52] U.S. Cl. ......................... 435/30; 435/320.1; 435/325; 435/366; 536/23.1; 536/23.5; 536/24.31; 536/24.33; 935/59; 935/60; 935/70

[58] Field of Search .............................. 514/44; 536/23.1, 536/23.5, 24.31, 24.33; 435/91.1, 320.1, 172.3, 320.01, 325, 366; 935/59, 60, 70

[56] References Cited

PUBLICATIONS

Hiller et al, Submitted Apr. 5, 1995, Accession No. R07162.
Hiller et al, Submitted May 24, 1995, Accession No. R60950.
Pronk, J.C. et al. Localisation of the Fanconi Anaemia Complementation Group A Gene to Chromosome 16q24.3. Nature Genetics, Nov. 1995, vol. 11, pp. 338–340, especially p. 339.
Hans Joenje, Ph.D., "Complementation Studies," *Fanconi Anemia Research Fund, Inc. Family Newsletter Scientific Supplement #20*: pp. 5, 12–13 (May 1996).
"Hans Joenje Receives FARF's Award of Merit," *Fanconi Anemia Research Fund, Inc. Family Newsletter #20*: pp. 1, 13 (Summer 1996).
Hans Joenje, Ph.D. (Ed.), *Eufar News No.5* (Jul. 1996).
R. Ishida and M. Buchwald, Anemia Lymphoblasts to DNA– cross–linking and Alkylating Agents, *Cancer Research* 42:4000–4006 (1982).
Duckworth–Rysiecki, et al., "Identification of Two Complementation Groups in Fanconi Anemia," *Somatic Cell and Molecular Genetics* 11:35–41 (1985).
Duckworth–Rysiecki, et al., "Characterization of a Simian virus 40–transformed Fanconi anemia fibroblast cell line," *Mutation Research* 166:207–214 (1986).
M.M. Gok and E. Wunder, "Microinjection of normal cell extracts into Fanconi anemia fibroblasts corrects defective scheduled DNA synthesis recovery after 8–methoxypsoralen plus UVa treatment," *Human Genetics* 75:350–355 (1987).
German, et al., "A Test for Fanconi's Anemia," *Blood* 69:1637–1641 (1987).
Buchwald, et al., "Studies of gene transfer and reversion to mitomycin C resistance in Fanconi anemia cells," *Mutation Research* 184:153–159 (1987).
Moustacchi, et al., "Two complementation groups of Fanconi's anemia differ in their phenotypic response to a DNA–crosslinking treatment," *Human Genetics* 75:45–47 (1987).
A.D. Auerbach, "A Test for Fanconi's Anemia," *Blood* 72:366–369 (1988).

Digweed, et al., "Complementation Studies in Fanconi Anemia Using Cell Fusion and Microinjection of mRNA," *Fanconi Anemia, Clinical, Cytogenetic and Experimental Aspects* (Schroeder–Kurth, et al., eds.) pp. 236–254 Springer–Verlag, Berlin (1989).
Buchwald, et al., "Complementation and Gene Transfer Studies in Fanconi Anemia," *Fanconi Anemia, Clinical, Cytogenetic and Experimental Aspects* (Schroeder–Kurth, et al., eds.) pp. 226–235 Springer–Verlag, Berlin (1989).
Auerbach, et al, "International Fanconi Anemia Registry: Relation of Clinical Symptoms to Diepoxybutane Sensitivity," *Blood* 73:391–396 (1989).
Auerbach, et al., "Complementation Studies in Fanconi Anemia," *Fanconi Anemia, Clinical, Cytogenetic and Experimental Aspects* (Schroeder–Kurth, et al., eds.) pp. 213–225 Springer–Verlag, Berlin (1989).
Tanaka, et al., "Molecular cloning of a mouse DNA repair gene that complements the defect of group–A xeroderma pigmentosum," *Proc. Natl. Acad. Sci. USA* 86:5512–5516 (1989).
Wunder, et al., "Cellular Effects of Fanconi Anemia Genes and Their Correction by Microinjecton," *Fanconi Anemia, Clinical, Cytogenetic and Experimental Aspects* (Schroeder–Kurth, et al., eds.) pp. 183–195 Springer–Verlag, Berlin (1989).
Rosenberg, et al., "Gene Transfer Into Humans—Immunotherapy of Patients with Advanced Melanoma, Using Tumor–Infiltrating Lymphocytes Modified by Retroviral Gene Transduction," *The New England Journal of Medicine* 323:570–578 (1990).
Teitz, et al., "Isolation by polymerase chain reaction of a cDNA whose product partially complements the ultraviolet sensitivity of xeroderma pigmentosum group C cells," *Gene* 87:295–298 (1990).
Tanaka, et al., "Analysis of a human DNA excision repair gene involved in group A xeroderma pigmentosum and containing a zinc–finger domain," *Nature* 348:73–76 (1990).
F. Rosselli and E. Moustacchi, "Cocultivation of Fanconi anemia cells and of mouse lymphoma mutants leads to interspecies complementation of chromosomal hypersensitivity to DNA cross–linking agents," *Human Genetics* 84:517–521 (1990).
Diatloff–Zito, et al., "Partial complementation of the Fanconi anemia defect upon transfection by heterologous DNA," *Human Genetics* 86:151–161 (1990).
Mann, et al., "Fanconi Anemia: Evidence for Linkage Heterogeneity on Chromosome 20q," *Genomics* 9:329–337 (1991).
Strathdee, et al., "Cloning of cDNAs for Fanconi's anaemia by functional complementation," *Nature* 356:763–767 (1992).
Espreafico et al (1992) J. Cell Biol. 119, 1541–1547.
Blau et al (Nov. 2, 1995) New Eng. J. Med. 1204–1207.

*Primary Examiner*—Deborah Crouch
*Attorney, Agent, or Firm*—Klarquist Sparkman Campbell Leigh & Whinston, LLP

[57] ABSTRACT

A cDNA molecule corresponding to the gene for human Fanconi anemia of complementation group A is disclosed. Also disclosed is the theoretical amino acid sequence of the FA-A protein. Methods of using these biological materials in the diagnosis and treatment of Fanconi anemia are presented.

8 Claims, 12 Drawing Sheets

FIG. 2A

```
AGCCGCCCGCC GGGGCTGTAG GCCGCCAAGGC CATGTCCGAC TCGTGGGTCC    50
                                    M  S  D     S  W  V

CGAACTCCGC CTCGGGCCAG GACCCAGGGG GCCGCCGGAG GGCCTGGGCC      100
 P  N  S  A  S  G  Q   D  P  G    G  R  R     A  W  A

GAGCTGCTGG CGGGAAGGGT CAAGAGGGAA AAATATAAATC CTGAAAGGGC     150
 E  L  L    A  G  R  V  K  R  E    K  Y  N     P  E  R  A

ACAGAAATTA AAGGAATCAG CTGTGCGCCT CCTGCGAAGC CATCAGGACC      200
 Q  K  L    K  E  S    A  V  R  L  L  R  S    H  Q  D

TGAATGCCCT TTTGCTTGAG GTAGAAGGTC CACTGTGTAA AAAATTGTCT      250
 L  N  A  L  L  L  E    V  E  G    P  L  C  K  K  L  S

CTCAGCAAAG TGATTGACTG TGACAGTTCT GAGGCCTATG CTAATCATTC      300
 L  S  K    V  I  D  C  D  S  S    E  A  Y     A  N  H  S

TAGTTCATTT ATAGGCTCTG CTTTGCAGGA TCAAGCCTCA AGGCTGGGGG      350
 S  S  F     I  G  S    A  L  Q  D  Q  A  S   R  L  G

TTCCCGTGGG TATTCTCTCA GCCGGGATGG TTGCCTCTAG CGTGGGACAG      400
 V  P  V  G  I  L  S    A  G  M    V  A  S  S  V  G  Q

ATCTGCACGG CTCCAGCGGA GACCAGTCAC CCTGTGCTGC TGACTGTGGA      450
 I  C  T    A  P  A  E  T  S  H    P  V  L    L  T  V  E

GCAGAGAAAG AAGCTGTCTT CCCTGTTAGA GTTTGCTCAG TATTTATTGG      500
 Q  R  K    K  L  S    S  L  L  E  F  A  Q     Y  L  L

CACACAGTAT GTTCTCCCGT CTTTCCTTCT GTCAAGAATT ATGGAAAATA      550
 A  H  S  M  F  S  R    L  S  F    C  Q  E  L  W  K  I
```

```
CAGAGTTCTT TGTTGCTTGA AGCGGGTGTGG CATCTTCACG TACAAGGCAT   600
 Q  S  S   L  L  E    A  V  W      H  L  H     V  Q  G  I
TGTGAGCCTG CAAGAGCTGC TGGAAAGCCA TCCCGACATG CATGCTGTGG    650
 V  S  L   Q  E  L    L  E  S  H  P  D  M    H  A  V
GATCGTGGCT CTTCAGGAAT CTGTGCTGCC TTTGTGAACA GATGGAAGCA    700
 G  S  W   L  F  R  N L  C  C    L  C  E  Q M  E  A
TCCTGCCAGC ATGCTGACGT CGCCAGGGCC ATGCTTTCTG ATTTTGTTCA    750
 S  C  Q   H  A  D  V A  R  A    M  L  S    D  F  V  Q
AATGTTTGTT TTGAGGGGAT TTCAGAAAAA CTCAGATCTG AGAAGAACTG    800
 M  F  V   L  R  G    F  Q  K  N S  D  L    R  R  T
TGGAGCCTGA AAAAATGCCG CAGGTCACGG TTGATGTACT GCAGAGAATG    850
 V  E  P   E  K  M  P Q  V  T    V  D  V  L Q  R  M
CTGATTTTTG CACTTGACGC TTTGGCTGCT GGAGTACAGG AGGAGTCCTC    900
 L  I  F   A  L  D  A L  A  A    G  V  Q    E  E  S  S
CACTCACAAG ATCGTGAGGT GCTGGTTCGG AGTGTTCAGT GGACACACGC    950
 T  H  K   I  V  R    C  W  F  G V  F  S    G  H  T
TTGGCAGTGT AATTTCCACA GATCCCTCTGA AGAGGTTCTT CAGTCATACC  1000
 L  G  S  V I  S  T   D  P  L     K  R  F  F S  H  T
CTGACTCAGA TACTCACTCA CAGCCCTGTG CTGAAAGCAT CTGATGCTGT   1050
 L  T  Q   I  L  T  H S  P  V    L  K  A    S  D  A  V
TCAGATGCAG AGAGAGTGGA GCTTTGCGCG GACACACCCT CTGCTCACCT   1100
 Q  M  Q   R  E  W    S  F  A  R T  H  P    L  L  T
CACTGTACCG CAGGCTCTTT GTGATGCTGA GTGCAGAGGA GTTGGTTGGC   1150
 S  L  Y  R R  L  F   V  M  L    S  A  E  E L  V  G
```

FIG. 2B

```
CATTGCAAG AAGTTCTGGA AACGCAGGAG GTTCACTGGC AGAGAGTGCT    1200
 H  L  Q   E  V  L  E   T  Q  E   V  H  W    Q  R  V  L
CTCCCTTGTG TCTGCCCTGG TTGTCTGCTT TCCAGAAGCG CAGCAGCTGC    1250
 S  F  V   S  A  L  V   V  C  F   P  E  A    Q  Q  L
TTGAAGACTG GGTGGCGCGT TTGATGGCCC AGGCATTCGA GAGCTGCCAG    1300
 L  E  D  W   V  A  R   L  M  A   Q  A  F  E   S  C  Q
CTGGACAGCA TGGTCACTGC GTTCCTGGTT GTGCGCCAGG CAGCACTGGA    1350
 L  D  S   M  V  T  A   F  L  V   V  R  Q    A  A  L  E
GGGCCCCTCT GCGTTCCTGT CATATGCAGA CTGGTTCAAG GCCTCCTTTG    1400
 G  P  S    A  F  L   S  Y  A  D   W  F  K    A  S  F
GGAGCACACG AGGCTACCAT GGCTGCAGCA AGAAGGCCCT GGTCTTCCTG    1450
 G  S  T  R   G  Y  H   G  C  S   K  K  A  L   V  F  L
TTTACGTTCT TGTCAGAACT CGTGCCTTTT GAGTCCTCCC GGTACCTGCA    1500
 F  T  F    L  S  E  L   V  P  F   E  S  P   R  Y  L  Q
GGTGCACATT CTCCACCCAC CCCTGGTTCC CAGCAAGTAC CGCTCCCTCC    1550
 V  H  I    L  H  P    P  L  V  P   S  K  Y   R  S  L
TCACAGACTA CATCTCATTG GCCAAGACAC GGCTGGCCGA CCTCAAGGTT    1600
 L  T  D  Y   I  S  L   A  K  T   R  L  A  D   L  K  V
TCTATAGAAA ACATGGGACT CTACGAGGAT TTGTCATCAG CTGGGGACAT    1650
 S  I  E   N  M  G  L   Y  E  D   L  S  S    A  G  D  I
TACTGAGCCC CACAGCCAAG CTCTTCAGGA TGTTGAAAAG GCCATCATGG    1700
 T  E  P   H  S  Q   A  L  Q  D   V  E  K    A  I  M
TGTTTGAGCA TACGGGAAAC ATCCCAGTCA CCGTCATGGA GGCCAGCATA    1750
 V  F  E  H   T  G  N   I  P  V   T  V  M  E   A  S  I
```

```
TTCAGGAGGC CTTACTACGT GTCCCACTTC CTCCCCGCCC TGCTCACACC   1800
 F  R  R    P  Y  Y  V    S  H  F    L  P  A    L  L  T  P
TCGAGTGCTC CCCAAAGTCC CTGACTCCCG TGTGGCGTTT ATAGAGTCTC   1850
 R  V  L    P  K  V    P  D  S  R    V  A  F    I  E  S
TGAAGAGAGC AGATAAAATC CCCCCATCTC TGTACTCCAC CTACTGCCAG   1900
 L  K  R  A    D  K  I    P  P  S    L  Y  S  T    Y  C  Q
GCCTGCTCTG CTGCTGAAGA GAAGCCAGAA GATGCAGCCC TGGGAGTGAG   1950
 A  C  S    A  A  E  E    K  P  E    D  A  A    L  G  V  R
GGCAGAACCC AACTCTGCTG AGGAGCCCCT GGGACAGCTC ACAGCTGCAC   2000
 A  E  P    N  S  A    E  E  P  L    G  Q  L    T  A  A
TGGGAGAGCT GAGAGCCTCC ATGACAGACC CCAGCCAGCG TGATGTTATA   2050
 L  G  E  L    R  A  S    M  T  D    P  S  Q  R    D  V  I
TCGGCACAGG TGGCAGTGAT TTCTGAAAGA CTGAGGGCTG TCCTGGGCCA   2100
 S  A  Q    V  A  V  I    S  E  R    L  R  A    V  L  G  H
CAATGAGGAT GACAGCAGCG TTGAGATATC AAAGATTCAG CTCAGCATCA   2150
 N  E  D    D  S  S    V  E  I  S    K  I  Q    L  S  I
ACACGCCGAG ACTGGAGCCA CGGGAACACA TTGCTGTGGA CCTCCTGCTG   2200
 N  T  P  R    L  E  P    R  E  H    I  A  V  D    L  L  L
ACGTCTTTCT GTCAGAACCT GATGGCTGCC TCCAGTGTCG CTCCCCCGGA   2250
 T  S  F    C  Q  N  L    M  A  A    S  S  V    A  P  P  E
GAGGCAGGGT CCCTGGGCTG CCCTCTTCGT GAGGACCATG TGTGGACGTG   2300
 R  Q  G    P  W  A    A  L  F  V    R  T  M    C  G  R
TGCTCCCTGC AGTGCTCACC CGGCTCTGCC AGCTGCTCCG TCACCAGGGC   2350
 V  L  P  A    V  L  T    R  L  C    Q  L  L  R    H  Q  G
```

```
CCGAGCCTGA GTGCCCCACA TGTGCTGGGG TTGGCTGCCC TGGCCGTGCA      2400
 P  S  L     S  A  P  H   V  L  G    L  A  A    L  A  V  H
CCTGGGTGAG TCCAGGTCTG CGCTCCCAGA GGTGGATGTG GGTCCTCCTG      2450
 L  G  E     S  R  S    A  L  P  E   V  D  V    G  P  P
CACCTGGTGC TGGCCTTCCT GTCCCTGCGC TCTTTGACAG CCTCCTGACC      2500
 A  P  G  A   G  L  P   V  P  A    L  F  D  S   L  L  T
TGTAGGACGA GGGATTCCTT GTTCTTCTGC CTGAAATTTT GTACAGCAGC      2550
 C  R  T     R  D  S  L   F  F  C    L  K  F    C  T  A  A
AATTCTTAC TCTCTCTGCA AGTTTCTTC CCAGTCACGA GATACTTTGT        2600
  I  S  Y    S  L  C    K  F  S  S    Q  S  R    D  T  L
GCAGCTGCTT ATCTCCAGGC CTTATTAAAA AGTTTCAGTT CCTCATGTTC      2650
 C  S  C  L   S  P  G    L  I  K    K  F  Q  F   L  M  F
AGATTGTTCT CAGAGGCCCG ACAGCCTCTT TCTGAGGAGG ACGTAGCCAG      2700
 R  L  F     S  E  A  R   Q  P  L    S  E  E    D  V  A  S
CCTTTCCTGG AGACCCTTGC ACCTTCCTTC TGCAGACTGG CAGAGAGCTG      2750
 L  S  W     R  P  L    H  L  P  S   A  D  W    Q  R  A
CCCTCTCTCT CTGGACACAC AGAACCTTCC GAGAGGTGTT GAAAGAGGAA      2800
 A  L  S  L   W  T  H    R  T  F    R  E  V  L   K  E  E
GATGTTCACT TAACTTACCA AGACTGGTTA CACCTGGAGC TGGAAATTCA      2850
 D  V  H     L  T  Y  Q   D  W  L    H  L  E    L  E  I  Q
ACCTGAAGCT GATGCTCTTT CAGATACTGA ACGGCAGGAC TTCCACCAGT      2900
 P  E  A     D  A  L    S  D  T  E   R  Q  D    F  H  Q
GGGCGGATCCA TGAGCACTTT CTCCCTGAGT CCTCGGCTTC AGGGGGCTGT     2950
 W  A  I  H   E  H  F    L  P  E    S  S  A  S   G  G  C
```

| | | | | |
|---|---|---|---|---|
| GACGGAGACC | TGCAGGCTGC | GTGTACCATT | CTTGTCAACG | CACTGATGGA | 3000
| D G D | L Q A A | C T I | L V N | A L M D |
| TTTCCACCAA | AGCTCAAGGA | GTTATGACCA | CTCAGAAAAT | TCTGATTTGG | 3050
| F H Q | S S R | S Y D H | S E N | S D L |
| TCTTTGGTGG | CCGCACAGGA | AATGAGGATA | TTATTCCAG | ATTGCAGGAG | 3100
| V F G G | R T G | N E D | I I S R | L Q E |
| ATGGTAGCTG | ACCTGGAGCT | GCAGCAAGAC | CTCATAGTGC | CTCTCGGCCA | 3150
| M V A | D L E L | Q Q D | L I V | P L G H |
| CACCCCTTCC | CAGGAGCACT | TCCTCTTTGA | GATTTTCCGC | AGACGGCTCC | 3200
| T P S | Q E H | F L F E | I F R | R R L |
| AGGCTCTGAC | AAGCGGGTGG | AGCGTGGCTG | CCAGCCTTCA | GAGACAGAGG | 3250
| Q A L T | S G W | S V A | A S L Q | R Q R |
| GAGCTGCTAA | TGTACAAACG | GATCCTCCTC | CGCCTGCCTT | CGTCTGTCCT | 3300
| E L L | M Y K R | I L L | R L P | S S V L |
| CTGCGGCAGC | AGCTTCCAGG | CAGAACAGCC | CATCACTGCC | AGATGCGAGC | 3350
| C G S | S F Q | A E Q P | I T A | R C E |
| AGTTCTTCCA | CTTGGTCAAC | TCTGAGATGA | GAAACTTCTG | CTCCCACGGA | 3400
| Q F F H | L V N | S E M | R N F C | S H G |
| GGTGCCCTGA | CACAGGACAT | CACTGCCCAC | TTCTTCAGGG | GCCTCCTGAA | 3450
| G A L | T Q D I | T A H | F F R | G L L N |
| CGCCTGTCTG | CGGAGCAGAG | ACCCCTCCCT | GATGGTCGAC | TTCATACTGG | 3500
| A C L | R S R | D P S L | M V D | F I L |
| CCAAGTGCCA | GACGAAATGC | CCCTTAATTT | TGACCTCTGC | TCTGGTGTGG | 3550
| A K C Q | T K C | P L I | L T S A | L V W |

FIG. 2G

```
TGGCCGAGCC TGGAGCCTGT GCTGCTCTGC CGGTGGAGGA GACACTGCCA         3600
 W  P  S     L  E  P  V     L  L  C     R  W  R     R  H  C  Q
GAGCCCGCTG CCCCGGGAAC TGCAGAAGCT ACAAGAAGGC CGGCAGTTTG         3650
 S  P  L     P  R  E     L  Q  K  L     Q  E  G     R  Q  F
CCAGGCGATTT CCTCTCCCCT GAGGCTGCCT CCCCAGCACC CAACCCGGAC        3700
 A  S  D  F     L  S  P     E  A  A     S  P  A  P     N  P  D
TGGCTCTCAG CTGCTGCACT GCACTTTGCG ATTCAACAAG TCAGGGAAGA         3750
 W  L  S     A  A  L     H  F  A     I  Q  Q     V  R  E  E
AAACATCAGG AAGCAGCTAA AGAAGCTGGA CTGCCGAGAGA GAGGAGCTAT        3800
 N  I  R     K  Q  L     K  K  L  D     C  E  R     E  E  L
TGGTTTTCCT TTTCTTCTTC TCCTTGATGG GCCTGCTGTC GTCACATCTG         3850
 L  V  F  L     F  F  F     S  L  M     G  L  L  S     S  H  L
ACCTCAAATA GCACCACAGA CCTGCCAAAG GCTTTCCACG TTTGTGCAGC         3900
 T  S  N     S  T  T  D     L  P  K     A  F  H     V  C  A  A
AATCCTCGAG TGTTTAGAGA AGAGGAAGAT ATCCTGGCTG GCACTCTTTC         3950
 I  L  E     C  L  E     K  R  K  I     S  W  L     A  L  F
AGTTGACAGA GAGTGACCTC AGGCTGGGGC GGCTCCTCCT CCGTGTGGCC         4000
 Q  L  T  E     S  D  L     R  L  G     R  L  L  L     R  V  A
CCGGATCAGC ACACCAGGCT GCTGCCTTTC GCTTTTTACA GTCTTCTCTC         4050
 P  D  Q     H  T  R  L     L  P  F     A  F  Y     S  L  L  S
CTACTTCCAT GAAGACGCGG CCATCAGGGA AGAGGCCTTC CTGCATGTTG         4100
 Y  F  H     E  D  A     A  I  R  E     E  A  F     L  H  V
```

FIG. 2H

```
CTGTGGACAT GTACTTGAAG CTGGTCCAGC TCTTCGTGGC TGGGGATACA      4150
 A  V  D  M   Y  L  K    L  V  Q    L  F  V  A   G  D  T
AGCACAGTTT CACCTCCAGC TGGCAGGAGC CTGGAGCTCA AGGGTCAGGG      4200
 S  T  V     S  P  P  A   G  R  S    L  E  L    K  G  Q  G
CAACCCCGTG GAACTGATAA CAAAAGCTCG TCTTTTTCTG CTGCAGTTAA      4250
 N  P  V    E  L  I     T  K  A  R   L  F  L    L  Q  L
TACCTCGGTG CCCGAAAAAG AGCTTCTCAC ACGTGGCAGA GCTGCTGGCT      4300
 I  P  R  C    P  K  K    S  F  S    H  V  A  E    L  L  A
GATCGTGGGG ACTGCGACCC AGAGGTGAGC GCCGCCCTCC AGAGCAGACA      4350
 D  R  G    D  C  D  P    E  V  S    A  A  L    Q  S  R  Q
GCAGGCTGCC CCTGACGCTG ACCTGTCCCA GGAGCCTCAT CTCTTCTGAC      4400
 Q  A  A    P  D  A     D  L  S  Q    E  P  H    L  F
GGGACCTGCC ACTGCACACC AGCCCAGCTC CCGTGTAAAT AATTTATTAC      4450
AAGCATAACA TGGAGCTCTT GTTGCACTAA AAAGTGGATT ACAAATCTCC      4500
TCGACTGCTT TAGTGGGGAA AGGAATCAAT TATTTATGAA CTGTCCGGCC      4550
CCGAGTCACT CAGCGTTTGC GGGAAAATAA ACCACTGGTC CCAGAGCAGA      4600
GGAAGGCTAC TTGAGCCGGA CACCAAGCCC GCCTCCAGCA CCAAGGGCGG      4650
GCAGCACCCT CCGACCCTCC CATGCGGGTG CACACGAAGG GTGAGGCTGA      4700
```

FIG. 2I

```
CACAGCCACT GCGGAGTCCA GGCTGCTAGA GGTGCTCATC CTCACTGCCG    4750
TCCTCAGGTG GGTTCGGGCT TCACCGCCTG GCCCCTCTGT GTCACAGAGG    4800
GGCTCGGTGG CCCAGGTGGT GGTTCCGCCT CCAGGGGCAG GGCCTTGTCC    4850
TGGGTCTGTG TCAGCGGGTG CACCATGGAC ATGTGTACAT TGAGGTTGTG    4900
GGCCTTCTCA AACCGCCGGC CACACTGGTC ACAGGCAAAG TCCAGCTCAG    4950
TCTCAGCCCT GTGTTTGGTC ATGTGGTACT TGAGGGATGC CCGCTGCCTG    5000
CACTGGAACC CACAGACCTC ACACCTGGGG GACAGAGGCA GATAAGAAGG    5050
TGCGAGGCCA CAGCCCTGGG AGGGGGTCCT GACTCACACT TACTGCAAAG    5100
GCTTGGCTCC CGAATGTCGC ATTTGGTGGA CGAGAAGGTG CTTCCGCTGC    5150
TTGAAGGTTT GTCCACATTC GTCACAGATA TAGTTCCGCA CCTCTGAGAG    5200
GGGAGAGTCC AGTGAGTCCA GGCCCCTGAT GCTCCAACCT CCCGGGGGA    5250
CGACGATGAC AATGTGAAAC CATCACAGCT GGGAAGACAT TTCTGCACAT    5300
```

```
GGTTCACCAT GCAGTGGGCC CAAGCAAGGG GCCTATGAGG GCCTCGTTTA    5350
TTAAGATCTT TAAACTGCTT TATACACTGT CACGTGGCTT CATCAGCTGT    5400
GTGCATTTCA GGATGGTTTT TAAAGAAACC TCAGAAAGCT ATTTCCTTAA    5450
AAAAAAAAAA AAAAAAAAAA AAAAAAAAAA AAAAAAAAAA AAAAAAAAAA    5500
AAA                                                      5503
```

FIG. 3

CDNA FOR FANCONI ANEMIA COMPLEMENTATION GROUP A

FIELD OF THE INVENTION

The present invention relates to the cloning and sequencing of the human cDNA molecule corresponding to the gene for Fanconi Anemia of complementation group A (FA-A). The present invention also relates to methods of screening for and detection of FA-A carriers, FA-A disease diagnosis, prenatal FA-A screening and diagnosis, and gene therapy utilizing recombinant DNA technologies.

BACKGROUND OF THE INVENTION

Fanconi Anemia (FA) is a rare and usually fatal human disorder characterized by progressive bone marrow failure, increased risk of malignancy and multiple congenital abnormalities mostly associated with developmental hypoplasia. It affects approximately one in 300,000 individuals (Swift, 1971).

The disorder may be associated with a variety of overt congenital somatic anomalies, such as hypoplasia or other malformations of the kidney, cutaneous hyperpigmentation, and bony abnormalities, particularly hypoplastic or absent thumbs and radii (Glanz and Fraser, 1982). However, these clinical manifestations of FA are extremely variable, both in type and severity, and so diagnosis of the disease on this basis alone is difficult and unreliable.

Affected individuals also show a range of gross hematological and immunological abnormalities: progressive pancytopenia with bone marrow hypoplasia (aplastic anemia), raised fetal hemoglobin and lymphopenia accompanied by defective mitogenic response to phytohaemagglutinin, and low natural killer cell function. Cells from FA patients exhibit a high level of spontaneous chromosomal aberrations when compared to cells of unaffected individuals. This cellular FA phenotype is even more apparent when DNA cross-linking agents such as mitomycin C (MMC) or diepoxybutane (DEB) are used to induce chromosome damage. Tests for prenatal and postnatal diagnoses of Fanconi Anemia have been developed based upon these cellular FA phenotypes. Schroeder et al. (1964, 1976) first suggested the use of spontaneous chromosomal breakage as a cellular marker for FA; however, longitudinal studies of chromosome instability in FA patients have shown a wide variation in the frequency of baseline breakage within the same individual, ranging from no baseline breakage to high levels (Schroeder et al., 1976; McIntosh et al., 1979). Chromosome breakage in response to DNA cross-linking agents were found to be a more reliable indicator of FA. Tests based on demonstrating an increased frequency of induced chromosomal breakage after exposure of cultured cells to a variety of DNA cross-linking agents such as MMC are in use in some laboratories (Berger et al., 1980; Cervenka et al., 1981), as are tests based on the differential inhibition of cell growth when FA and normal lymphocytes are cultured in a medium containing MMC (Arwert and Kwee, 1989). Prenatal and postnatal diagnoses of FA are also made based upon an analysis of DEB-induced chromosomal breakage as described by Auerbach et al. (1989a). This DEB hypersensitivity is now a widely accepted criterion in the diagnosis of FA.

The finding of a positive diagnosis of FA is critically important in determining an appropriate treatment regime. Data from the International Fanconi Anemia Registry (IFAR) show that at least 25% of FA patients have no congenital malformations (Auerbach et al., 1989b). Thus, individuals with aplastic anemia or leukemia but with no overt clinical manifestations of FA may be FA sufferers. Bone marrow transplantation is frequently used to treat aplastic anemia and, as part of this treatment, cyclophosphamide (a neoplastic suppressant) may be administered; FA patients are hypersensitive to this agent because of their susceptibility to DNA cross-linking agents, and so routine administration of cyclophosphamide to FA patients may be dangerous. Similarly, FA patients are hypersensitive to the chemotherapeutic agents that may be employed in treating leukemia. It has therefore been suggested that all young patients with aplastic anemia or leukemia of unknown etiology should be tested for sensitivity to DEB in order to rule out a diagnosis of FA (Auerbach et al., 1989a).

Studies have shown that FA is a recessive autosomal disorder. That is, it is an inherited disease which results from the presence of a mutated gene in both parents. Briefly put, a gene which, when mutated, gives rise to FA in an individual may be referred to as an FA gene. Human cells are diploid, meaning that each cell has two copies of each chromosome and therefore two copies of each gene including each FA gene, one contributed from each parent. The recessive nature of the FA disorder means that both copies of a particular FA gene must be mutated in order for an individual to exhibit symptoms. Thus, it is assumed that FA sufferers carry one (or more) mutation(s) in both copies of a particular FA gene. A non-mutated, normal version of this gene encodes a protein that plays a role in a particular biochemical pathway of the cell. The normal protein is therefore required for overall normal cell function. The mutated FA gene encodes either a defective protein or no protein at all, and so the specific biochemical pathway for which the portion is required is changed, and thereby normal cell function is disrupted. Individuals who have one copy of an FA gene which is "normal" and one copy which is mutated do not exhibit FA symptoms but rather, are FA carriers. FA carriers may also be described as FA heterozygotes. It is thus proposed that FA heterozygotes do not manifest clinical FA symptoms because they have one normal copy and one mutant copy of a particular FA gene, and that the protein produced by the one normal gene is sufficient for normal cell function (or at least sufficiently normal cell function so that no overt clinical abnormalities are presented). The offspring of two FA carriers who carry mutations in the same FA gene have a 25 percent chance of inheriting the FA disease and a 50 percent chance of being FA carriers themselves.

Parental heterozygotes of FA patients are superficially normal in appearance and lack overt laboratory abnormalities. Various attempts have been made to correlate FA heterozygote status to definite clinical symptoms and also to provide a direct laboratory test for heterozygosity. A reliable test for FA carrier status (FA heterozygotes) would be of great benefit for genetic counseling generally and most particularly for families with a history of Fanconi Anemia. A reliable test for heterozygotes would also greatly aid the development of treatment regimes for FA sufferers. Left to follow its natural course, FA is always fatal, with death caused by progressive bone marrow aplasia or, less frequently, by development of acute leukemia.

Bone marrow transplantation (BMT) has the potential to correct the stem cell defect and offers a reasonable chance of cure if a tissue-matched healthy donor can be located. It is mandatory to assess potential donors with respect to their FA status. The determination that a potential donor is an FA heterozygote may direct against the selection of tissues from this donor if alternative donors are available. Tissue-matched donors are most likely to be found among close family members of the patient, and there is clearly an increased risk that potential donors who are family members will be either FA sufferers or FA heterozygotes.

Auerbach and Wolman (1978) proposed the use of the DEB test to detect heterozygotes. However, as described by Dallapiccola and Porfirio (1989), the DEB-induced chromosomal breakage rate has been shown to be similar in FA heterozygotes and normal individuals, severely limiting the use of this test. Berger et al. (1980) have proposed the use of Sister Chromatid Exchange Analysis (SCE) in conjunction with exposure to nitrogen mustard gas, although the reliability of this test has also been questioned (Dallapiccola and Porfirio, 1989). Petridou and Barrett (1990) have suggested that FA heterozygotes show minor physical and hematological abnormalities perhaps consistent with partial expression of an FA gene in the heterozygote. However, the subtlety and inherent variation of these "symptoms" may make a clinically reliable diagnosis of FA heterozygosity based on these abnormalities difficult.

As the foregoing description illustrates, it has not been possible to satisfactorily identify heterozygote carriers of a mutant FA gene either at the clinical level or through direct laboratory tests. There is a widely recognized need for such a test, which has been articulated by researchers in this area. Dallapiccola and Porfirio (1989), for example, remarked that:

In the last decade, efforts to develop in vitro tests for the identification of FA heterozygotes have not been successful. No study has provided accurate and reliable tests with obligate heterozygotes. Even the DEB test— which gives reproducible results in the diagnosis of FA homozygotes and also shows a rather distinct clastogenic effect in a proportion of heterozygotes—does not meet widely accepted criteria for a screening test in the population. The other laboratory tests, which are also based upon the presumed ability of different chemicals to induce differential yields of breaks and/or in FA heterozygotes and controls, provide even less satisfactory results. There is an urgent need to improve laboratory tests for the study of FA heterozygotes.

Intensive research has been in progress to find a suitable laboratory test to fill the need.

Although the heritable characteristics of the disease are recognized, the exact underlying basis for FA is still unknown. The determination of the exact underlying defect in FA is complicated by the widely varying symptoms of the disease. Two hypotheses have been proposed for the possible biochemical defect based upon the observation of increased sensitivity to DNA cross-linking agents of FA cells. The first proposes that FA cells cannot repair damaged DNA because the defective protein is directly involved in recognizing, modifying or repairing cross links. The alternative hypothesis is that the cell is unable to respond to the oxidative stress caused by DNA cross-linking agents because of a defect in one of the detoxification mechanisms that remove free radicals or oxygen byproducts.

Research has also been directed toward determining the number of genes which, when mutated, can give rise to FA. To date, five FA complementation groups (A–E) have been established based on somatic cell hybridization experiments (Duckworth-Rysiecki et al., 1985; Strathdee et al., 1992(a); Joenje et al., 1995). Briefly put, assuming multiple FA genes, if a first FA cell line is homozygous for a mutation in FA gene #1, it will produce a corresponding defective FA protein #1 and be unable to perform the biochemical function normally provided by FA protein #1. Similarly, if a second FA cell line is homozygous for a mutation in FA gene #2, it will produce a corresponding defective FA protein #2 and be unable to perform the biochemical function normally provided by FA protein #2. Both of these cell lines will therefore exhibit sensitivity to DNA cross-linking agents characteristic of FA cell lines. When these two cell lines are then fused together (a process known as somatic cell hybridization), the resulting somatic cell hybrid will contain functional FA protein #1 (from FA cell line #2) and functional FA protein #2 (from FA cell line #1). This somatic hybrid will therefore be able to perform both biochemical functions and will exhibit the characteristics of normal cells rather than the characteristics of FA cells. Thus, FA gene #1 and FA gene #2 are said to "complement" each other and to belong to different "complementation groups."

Although the possibility of intragenic complementation has not been ruled out, the finding of five different FA complementation groups suggests that there might be five different FA genes, mutations in any one of which could give rise to the FA disease. Notably, the FA-A complementation group accounts for over 65% of all FA patients analyzed (Buchwald, 1995; Joenje, 1996).

Recently, a cDNA for the FA gene corresponding to complementation group C (FA-C) was cloned and located to position q22.3 on chromosome 9 (Strathdee et al., 1992a, 1992b; WO 93/22435), and genetic map positions of the FA-A and FA-D genes were reported (Pronk et al., 1995; Whitney et al., 1995). Such progress brings the possibility of DNA-based diagnosis and therapy for Fanconi Anemia significantly closer.

It is the object of the present invention to provide a human cDNA molecule for the FA-A complementation group, which group appears to represent the majority of Fanconi Anemia sufferers. The cloning and sequencing of such a cDNA molecule should facilitate new and improved methods of diagnosis and treatment of Fanconi Anemia.

SUMMARY OF THE INVENTION

The foregoing object has been achieved by providing an isolated human cDNA molecule which is able specifically to correct the cellular defect characteristic of cells from patients with Fanconi Anemia of complementation group A. Specifically, the invention provides, for the first time, an isolated cDNA molecule which, when transfected into cells derived from a patient with FA of complementation group A is able to complement the hypersensitivity to DNA cross-linking agents, such as mitomycin C (MMC), exhibited by these cells. The invention encompasses this FA-A cDNA molecule (derived from healthy (non-FA) human cells), the nucleotide sequence of this cDNA and the putative amino acid sequence of the FA-A protein encoded by this cDNA.

Having herein provided the nucleotide sequence of the FA-A cDNA, correspondingly provided are the complementary DNA strands of the cDNA molecule and DNA molecules which hybridize under stringent conditions to the FA-A cDNA molecule or its complementary strand. Such hybridizing molecules include DNA molecules differing only by minor sequence changes, including nucleotide substitutions, deletions and additions. Also comprehended by this invention are isolated oligonucleotides comprising at least a segment of the cDNA molecule or its complementary strand, such as oligonucleotides which may be employed as effective DNA hybridization probes or primers useful in the polymerase chain reaction or as hybridization probes. Such probes and primers are particularly useful in diagnosis of FA-A carriers and sufferers.

Hybridizing DNA molecules and variants on the FA-A cDNA may readily be created by standard molecular biology techniques. Through the manipulation of the nucleotide sequence of the human cDNA provided by this invention by standard molecular biology techniques, variants of the FA-A protein may be made which differ in precise amino acid sequence from the disclosed protein yet which maintain the essential characteristics of the FA-A protein or which are selected to differ in one or more characteristics from this protein. Such variants are another aspect of the present invention.

Also provided by the present invention are recombinant DNA vectors comprising the disclosed DNA molecules, and transgenic host cells containing such recombinant vectors.

Having provided the isolated human FA-A cDNA sequence, also comprehended by this invention is the genomic gene from which this cDNA is derived. The present invention also provides for the use of the FA-A cDNA, the corresponding genomic gene and derivatives thereof, and of the FA-A protein, and derivatives thereof, in aspects of diagnosis and treatment of FA-A.

An embodiment of the present invention is a method for screening a subject to determine if said subject carries a mutant FA-A gene. The method comprises the steps of: providing a biological sample obtained from the subject, which sample includes DNA or RNA, and providing an assay for detecting in the biological sample the presence of a mutant FA-A gene or a mutant FA-A RNA. This assay preferably comprises either: hybridization with oligonucleotides; PCR amplification of the FA-A gene or a part thereof using oligonucleotide primers; RT-PCR amplification of the FA-A RNA or a part thereof using oligonucleotide primers; or direct sequencing of the FA-A gene of the subject's genome using oligonucleotide primers. The efficiency of these molecular genetic methods should permit a more rapid classification of FA patients than is possible with the labor intensive method of classical complementation analysis.

A further aspect of the present invention is a method for screening a subject to assay for the presence of a mutant FA-A gene comprising the steps of: providing a biological sample of the subject which sample contains cellular proteins and providing an immunoassay for quantitating the level of FA-A protein in the biological sample. Diagnostic methods for the detection of mutant FA-A genes made possible by this invention will add to molecular diagnostic methods made possible by the earlier discovery of the FA-C cDNA and provide physicians with an enhanced ability to diagnose FA.

Another aspect to the present invention is an antibody preparation comprising antibodies that specifically detect the FA-A protein, wherein the antibodies are selected from the group consisting of monoclonal antibodies and polyclonal antibodies.

Those skilled in the art will appreciate the utility of this invention which is not limited to the specific experimental modes and materials described herein.

The foregoing and other features and advantages of the invention will become more apparent from the following detailed description and accompanying drawings.

BRIEF DESCRIPTION OF THE DRAWINGS

FIG. 2 shows the nucleotide sequence of the FA-A cDNA insert of the complementing clone D. An open reading frame starts at the first ATG (position 32) and ends at position 4,399 with a TGA stop codon, predicting a protein of 1,455 amino acids. This sequence is shown as Seq. ID No. 1 in the accompanying Sequence Listing.

FIG. 3 shows the amino acid sequence of predicted FA-A protein. Amino acids are indicated in single letter codes. This sequence is shown as Seq. ID No. 2 in the accompanying Sequence Listing, in 3 letter code.

SEQUENCE LISTING

Figure 1:
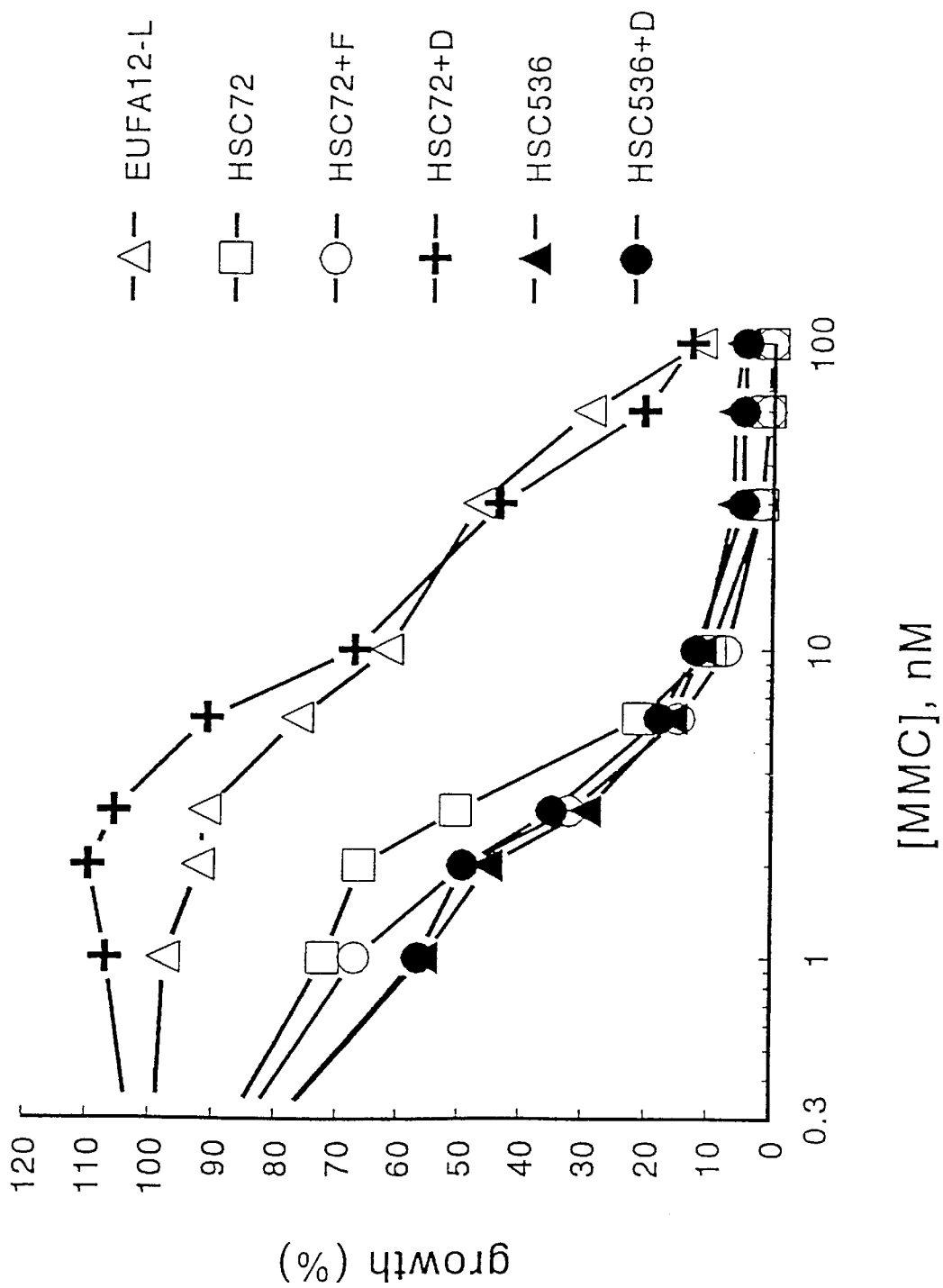
FIG. 1 shows MMC-induced growth inhibition tests showing complementation of crosslinker hypersensitivity by clone D DNA. Hypersensitivity of HSC72 (FA-A) lymphoblasts was restored to the level observed in wild-type cells after transfection with clone D, but not with clone F DNA. Complementation was specific for group A, since clone D DNA failed to correct HSC536 (FA-C) lymphoblasts. EUFA12, lymphoblasts from a healthy control.

In the accompanying sequence listing:
  Seq. I.D. No. 1 shows the nucleotide sequence of the FA-A cDNA;
  Seq. I.D. No. 2 shows the amino acid sequence of the predicted FA-A protein;
  Seq. I.D. Nos. 3–14 show PCR primers utilized in mutational analyses;
  Seq. I.D. Nos. 15–18 show PCR primers that may be used to amplify the FA-A cDNA.

DEFINITIONS

In order to facilitate review of the various embodiments of the invention and an understanding of various embodiments and constituents used in making the invention, the following definition of terms is provided:

BMT: bone marrow transplantation.

DNA: deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

cDNA (complementary DNA): a piece of DNA lacking internal, non-coding segments (introns) and regulatory sequences which determine transcription. cDNA is synthesized in the laboratory by reverse transcription from messenger RNA extracted from cells.

FA: Fanconi Anemia.

FA carrier or FA heterozygote: a person who does not exhibit apparent signs and symptoms of FA but whose chromosomes contain a mutant FA gene that may be transmitted to that person's offspring.

FA gene: a gene, the mutant forms of which are associated with the disease Fanconi Anemia. This definition is understood to include the various sequence polymorphisms that exist, wherein nucleotide substitutions in the gene sequence do not affect the essential functions of the gene product. This term relates primarily to an isolated coding sequence, but can also include some or all of the flanking regulatory elements and/or intron sequences.

FA patient: a person who carries a mutant FA gene on each chromosome, such that the person exhibits clinical signs and/or symptoms of FA.

FA-A: Fanconi Anemia of complementation group A.

FA-C: Fanconi Anemia of complementation group C.

FA-A carrier or FA-A heterozygote: a person who does not exhibit signs or symptoms of FA but whose chromosomes contain a mutant FA-A gene that may be transmitted to that person's offspring.

FA-A gene: the gene, present in the human genome, mutant forms of which are associated with Fanconi Anemia of complementation group A. This definition is understood to include the various sequence polymorphisms that exist, wherein nucleotide substitutions in the gene sequence do not affect the essential functions of the gene product. This term relates primarily to an isolated coding sequence, but can also include some or all of the flanking regulatory elements and/or intron sequences.

FA-A patient: a person who carries a mutant FA-A gene on each chromosome, such that the person exhibits clinical symptoms of FA-A.

FA-A cDNA: a human cDNA molecule which, when transfected into FA-A cells, is able to complement the hypersensitivity of those cells to DNA crosslinking agents. The FA-A cDNA is derived by reverse transcription from the mRNA encoded by the FA-A gene and lacks internal non-coding segments and transcription regulatory sequences present in the FA-A gene.

FA-A protein: the protein encoded by the human FA-A cDNA. This definition is understood to include the various sequence polymorphisms that exist, wherein amino acid substitutions in the protein sequence do not affect the essential functions of the protein.

Isolated: requires that the material be removed from its original environment. For example, a naturally occurring DNA molecule present in a living animal is not isolated, but the same DNA molecule, separated from some or all of the coexisting materials in the natural system, is isolated.

Mutant FA-A gene: a mutant form of the FA-A gene which is associated with Fanconi Anemia of complementation group A.

Mutant FA-A RNA: the RNA transcribed from a mutant FA-A gene.

Mutant FA-A protein: the protein encoded by a mutant FA-A gene.

ORF: open reading frame. Contains a series of nucleotide triplets (codons) coding for amino acids without any termination codons. These sequences are usually translatable into protein.

PCR: polymerase chain reaction. Describes a technique in which cycles of denaturation, annealing with primer, and then extension with DNA polymerase are used to amplify the number of copies of a target DNA sequence.

Protein: a biological molecule expressed by a gene and comprised of amino acids.

Purified: the term "purified" does not require absolute purity; rather, it is intended as a relative term. Thus, for example, a purified protein preparation is one in which the protein referred to is more pure than the protein in its natural environment within a cell.

VNTR probes: Variable Number of Tandem Repeat probes. These are highly polymorphic DNA markers for human chromosomes. The polymorphism is due to variation in the number of tandem repeats of a short DNA sequence. Use of these probes enables the DNA of an individual to be distinguished from that derived from another individual.

Additional definitions of common terms in molecular biology may be found in Lewin, B. "Genes IV" published by Oxford University Press.

DETAILED DESCRIPTION OF THE INVENTION

Materials and Methods

Patients and Cell Lines

HSC72 and HSC536 are the reference lymphoblastoid cell lines for groups A and C, respectively (Duckworth-Rysiecki et al., 1985; Strathdee et al., 1992a; Joenje et al., 1995); the patients have been described previously by Buchwald et al. (1989), as FA1 (HSC72) and FA8 (HSC536). Patients VU373, EUFA007, EUFA275 and EUFA471 were assigned to complementation group A on the basis of non-complementation in fusion hybrids with HSC72 cells (Joenje et al., 1995). EUFA12 is a healthy control individual.

Manipulation of Genetic Material

Unless otherwise specified, manipulation of genetic material was performed according to standard laboratory procedures, such as those described in Sambrook et al. (1989) and Ausubel et al. (1987).

Isolation of the FA-A cDNA

The FA-A cDNA was isolated using genetic complementation. Essentially, cultured lymphoblastoid cells from a patient with Fanconi Anemia of complementation group A were transfected with a cDNA expression library derived from a healthy individual. After confirming successful and stable transfection, the cells were then exposed to the crosslinking agent mitomycin C (MMC). FA-A cells are sensitive to crosslinking agents such as MMC and are, ordinarily, unable to survive in the presence of these substances. However, those cells transfected with a normal version of the FA-A cDNA are able to survive the MMC treatment because their inherent sensitivity to MMC is complemented by the normal FA-A protein encoded by the transfected DNA. Accordingly, cells that remain viable after the MMC treatment may then be selected and the transfected material within those cells further characterized.

More specifically, the complementation method utilized is that previously described by Strathdee et al. (1992b) and also set forth in WO 93/22435, which publications are herein incorporated by reference. Essentially, a human cDNA library was constructed in pREP4 (Groger et al., 1989) using the Moloney Murine Leukemia Virus-RNaseH$^-$ reverse transcriptase (BRL) in conjunction with vector primed synthesis to enhance the yield of full-length inserts oriented with respect to the Rous Sarcoma Virus (RSV)-3'Long Terminal Repeat (LTR) promoter and SV40 polyadenylation signal. The pREP4 vector contains hygromycin and ampicillin resistance markers for selected propagation in mammalian cells and *E. coli*, respectively. This vector also includes the ColE1 bacterial origin of replication required for replication in prokaryotes and is maintained episomally in lymphoblasts, which permits recovery of plasmids by extraction of low molecular weight DNA and subsequent transfer into bacteria.

Complementation group A lymphoblasts HSC72 (Duckworth-Rysiecki et al., 1985) were transfected with this human cDNA-pREP4 library by electroporation as described by Kruyt et al., (1996). Following selection for library uptake (200 µg hygromycin/ml for 2 weeks) and crosslinker resistance (6 nM MMC, 6 weeks), a surviving cell population was obtained that exhibited a wild type level of resistance to MMC and was fully crossresistant to the cross-linkers diepoxybutane (DEB) and cis-diamminedichloroplatinum(II). About 20% of the plasmids recovered appeared intact and had inserts. Thirty independent intact clones were pooled and used for a second round of transfection and MMC selection, again resulting in a population of cells resistant to all 3 crosslinkers. Restriction mapping of the intact recovered plasmids indicated the presence of 8 different inserts, termed clone A–H. Individual clones were transfected into HSC72 cells and checked for complementation. Only one clone was identified (clone D) that corrected crosslinker hypersensitivity of FA-A cells, but not of FA-C cells (FIG. 1).

Sequence Analysis of Clone D

Restriction mapping of clone D revealed that it contained a 5.5 kb cDNA insert. Sequencing of this insert using conventional DNA sequence methods revealed that it contained a 4368 nucleotide open reading frame (ORF), a 31 nucleotide 5' untranslated region (UTR) and 1.1 kb 3' UTR (FIG. 2a). The ORF predicts a 1,455 amino acid protein with a relative molecular mass of 162,752, based on the first ATG at position 34 (FIG. 2b). The second ATG, at position 377, might be an alternative start, since neither of these codons have a clear Kozak consensus sequence. Also, a clear polyadenylation signal is lacking from the 3' UTR. In vitro transcription/translation of the full-length cDNA yielded a product of approximately 160 kD (results not shown) as well as shorter products consistent with alternative in vitro translation start sites. In vitro translation products in two FA-A families showed segregation of a truncated polypeptide with the disease trait.

Secondary structure prediction of the FA-A protein revealed a high content of alpha helix (Kneller et al. 1990). A PROSITE search for motifs (Bairoch 1991) indicated two overlapping bipartite nuclear localization signals (Dingwall and Laskey 1991), located at amino acids 18–34 and 19–35, suggesting that the FA-A polypeptide, in contrast to the FA polypeptide, might be a nuclear protein. In addition, a partial leucine zipper consensus sequence was located in the region 1069–1090. The consensus pattern is limited to the L(6)L(6)L(6)L portion, which forms the dimerization domain, but lacks the basic region which interacts directly with DNA (reviewed in Hurst, 1994). No significant homologies to either FA-A necleotide or protein sequences were detected by searching common databases using the BLAST algorithm (Altschul et al. 1990).

Northern Blot Analysis

Northern blot analysis of FA-A RNA expression in lymphoblastoid cell lines showed the presence of a band of approximately 5.5 kb in non-FA cells as well as FA cells from various non-A complementation groups. In two cell lines assigned to complementation group A, the amounts of the 5.5 kb transcript were lower than in control or non FA-A cell lines, suggesting the presence of mutations which either reduce transcription or reduce the stability of the mRNA.

Confirmation that Clone D is the FA-A cDNA

To confirm that the cDNA contained within clone D does indeed represent the FA-A cDNA, cell lines from Fanconi Anemia patients classified as FA-A by complementation analysis were screened for mutations in this gene. Two types of tests were used in these analyses: protein truncation (PTT) and single strand confirmational polymorphism (SSCP). For each of these tests, RNA was isolated from lymphoblastoid cells using Trizol reagent (Life Technologies) and cDNA was prepared using Superscript reverse transcriptase (Life Technologies) and oligodTlo primers (Boehringer).

The PTT test was performed essentially as described by Hogervorst et al. (1995). The 5' region of the FA-A gene was amplified in two overlapping fragments using sense primers with incorporated T7 promoter sequences. Primer combinations were as follows:

```
Combination 1:
5'-GCGTAATACGACTCACTATAGGGATGGTTGCCTCTAGCGTGGGAC-3'     (Seq. I.D. No. 3)
(sense, position 376); and 5'-TGATATCTCAACGCTGCTGTCAT-3'                            (Seq. I.D. No. 4)
(Antisense, position 2109).

Combination 2:
5'-CGCTAATACGACTCACTATAGGAACAGACCACCATGGCCATCATGGTGTTTG  (Seq. I.D. No. 5)
AGCATAC-3'  (sense, position 1690);

and

5'-CCGAGGACTCAGGGAGAAAGTGCTCA-3'                         (Seq. I.D. No.6)
(antisense, position 2909).
```

PCR products were in vitro transcribed/translated in the TNT T7 Coupled Reticulocyte Lysate System (Promega) in the presence of $^{3}$S-methionine (Redivue, Amersham). Proteins were separated on a 15% SDS polyacrylamide gel, with 4% stacking gel using a Hoefer Might Small electrophoresis system. After electrophoresis, the gel was fixed in two changes of 25% isopropanol/10% acetic acid for 20 and 60 min, respectively, and dried. Detection of $^{35}$S-labelled proteins was performed with a GS-363 Molecular Imager System (BioRad).

The SSCP/Heteroduplex test was performed essentially as follows: first, the 5' part of the FA-A coding region was amplified in 4 overlapping fragments of about 600 bp. These products were checked by gel electrophoresis for their size in order to detect deletions or alternatively spliced transcripts. Then, the PCR products were digested with a restriction enzyme generating 2 fragments of about 300 bp. The following primer combinations were used:

```
Primer Combination 1:
5'-TGTTCTCCCGTCTTTCCTTC-3'     (Seq. I.D. No. 7)      (510);

5'-GTGAGCAGAGGGTGTGTC-3'       (Seq. I.D. No. 8)      (1081)
product cut with BglII Primer Combination 2:
5'-GTTCGGAGTGTTCAGTGGAC-3'     (Seq. I.D. No. 9)      (924)

5'-GGGTGGGGTGGAGAATGTG-3'      (Seq. I.D. No. 10)     (1505)
product cut with TaqI
```

```
Primer Combination 3:
5'-GGCCCTGGTCTTCCTGTTTA-3'    (Seq. I.D. No. 11)   (1435)

5'-CCTCAGCAGAGTTGGGTTCT-3'    (Seq. I.D. No. 12)   (1954)
product cut with PvuII Primer Combination 4:
5'-GACTCCCGTGTGGCGTTTAT-3'    (Seq. I.D. No. 13)   (1823)

5'-CAGCACATGTGGGGCACTCA-3'    (Seq. I.D. No. 14)   (2358)
product cut with EcoRI.
```

The results of these mutational analyses are shown in Table 1. As shown in this Table, different sequence variations were encountered in patients from different ancestral backgrounds. The variations were likely to be pathogenic on the basis of their severity and their segregation with the disease in 3 informative multiplex families. These data confirmed that the cDNA indeed represented the FA-A gene.

TABLE 1

Mutations in 4 FA-A Patients

| Patient Code | Ancestry | Mutation Description | Predicted Consequence |
|---|---|---|---|
| EUFA007[a] | Germany | 1391del467 | truncated protein of 455 aa (453 + S + R)[c] |
| EUFA275[a] | Spain | 740 + 5G –> A[d] | D237G + 237ins10 (AFMTRCGFLD) |
| VU373[b] | Egypt | 740 + 5G – T[d] | D237G + 238ins10 (AFMTRCGFLD) |
| EUFA471[a] | Guatamala | 1932del879 | D534V, 635del293[c] |

[a]Multiplex families, in which a mutated allele segregated with the disease phenotype. Patients in these families were apparently compound heterozygotes for different mutations, only one of which was resolved as indicated.
[b]This patient, from a consanguineous marriage, was homozygous for this splice site mutation and identical to an affected sib.
[c]Confirmed by the protein truncation test. The mutation in patient EUFA471 was also confirmed by PCR of a genomic DNA fragment encompassing the deletion.
[d]Splice site mutation causing utilization of a downstream cryptic splice site (gg/gtaaaa) leading to insertion of 30 bp of intronic sequence.

Preferred Method of Making the FA-A cDNA

The foregoing discussion describes the original means by which the FA-A cDNA was obtained and also provides the nucleotide sequence of this clone. With the provision of this sequence information, the polymerase chain reaction (PCR) may now be utilized in a more direct and simple method for producing the FA-A cDNA.

Essentially, total RNA is extracted from human cells by any one of a variety of methods routinely used; Sambrook et al. (1989) and Ausubel et al. (1987) provide descriptions of methods for RNA isolation. Any human cell line derived from a non-FA individual would be suitable, such as the widely used HeLa cell line, or the WI-38 human skin fibroblast cell line available from the American Type Culture Collection, Rockville, Md. The extracted RNA is then used as a template for performing the reverse transcription-polymerase chain reaction (RT-PCR) amplification of cDNA. Methods and conditions for RT-PCR are described in Kawasaki et al. (1990). The selection of PCR primers will be made according to the portions of the cDNA which are to be amplified. Primers may be chosen to amplify small segments of a cDNA or the entire cDNA molecule. Variations in amplification conditions may be required to accommodate primers of differing lengths; such considerations are well known in the art and are discussed in Innis et al. (1990). The entire FA-A cDNA molecule may be amplified using the following combination of primers:

```
primer 1 5' AGCCGCCGCCGGGGCTGTAGGCGC 3'   (Seq. I.D. No. 15)
primer 2 5' TAAGGAAATAGCTTTCTGAGGTTT 3'   (Seq. I.D. No. 16)
```

The open reading frame of the cDNA molecule may be amplified using the following combination of primers:

```
primer 1 5' ATGTCCGACTCGTGGGTCCCGAACTCC 3'   (Seq. I.D. No. 17)
primer 2 5' TCAGAAGAGATGAGGCTCCTGGGACAG 3'   (Seq. I.D. No. 18)
```

These primers are illustrative only; it will be appreciated by one skilled in the art that many different primers may be derived from the provided cDNA sequence in order to amplify particular regions of these cDNAs.

Cloning of the FA-A Genomic Gene

The FA-A cDNA sequence described above does not contain the introns, upstream transcriptional promoter or regulatory regions or downstream transcriptional regulatory regions of the FA-A gene. It is possible that some mutations in the FA-A gene that may lead to FA are not included in the cDNA but rather are located in other regions of the FA-A gene. Mutations located outside of the open reading frame that encodes the FA-A protein are not likely to affect the functional activity of the protein but rather are likely to result in altered levels of the protein in the cell. For example, mutations in the promoter region of the FA-A gene may prevent transcription of the gene and therefore lead to the complete absence of the FA-A protein in the cell.

Additionally, mutations within intron sequences in the genomic gene may also prevent expression of the FA-A protein. Following transcription of a gene containing introns, the intron sequences are removed from the RNA molecule in a process termed splicing prior to translation of the RNA molecule which results in production of the encoded protein. When the RNA molecule is spliced to remove the introns, the cellular enzymes that perform the splicing function recognize sequences around the intron/exon border and in this manner recognize the appropriate splice sites. If there is a mutation within the sequence of the intron close to the junction of the intron with an exon, the enzymes may not recognize the junction and may fail to remove the intron. If this occurs, the encoded protein will likely be defective. Thus, mutations inside the intron sequences within the FA-A gene (termed "splice site mutations") may also lead to FA. It is known that shortened transcripts of the FA-C RNA have been detected in several patients with Fanconi Anemia of complementation group C. Such shortened transcripts may be the result of splice-site mutations. However, knowledge of the exon structure and intronic splice site sequences of the FA genes is required to define the molecular basis of these abnormalities.

Furthermore, as a consequence of the pancytopenia found in FA patients and the poor growth characteristics of FA cell-lines, only genomic DNA is available from the majority of patients. Efficient screening of the FA-A gene for mutations in these patients by PCR amplification of genomic DNA will require knowledge of the exon structure and adjacent intron sequences of the gene.

The provision herein of the FA-A cDNA sequence enables the cloning of the entire FA-A gene (including the promoter and other regulatory regions and the intron sequences) and the determination of its nucleotide sequence. With this information in hand, diagnosis of FA carrier/sufferer status based on DNA analysis will comprehend all possible mutagenic events at the FA-A locus. The cloning of the entire FA-A gene may be accomplished by the methods used to clone the FA-C gene, as described in WO 93/22435. Essentially, a YAC library of human genomic sequences (Monaco and Lehrach, 1991) is screened for the FA-A gene by the polymerase chain reaction (PCR). The library is arranged in a number (e.g., 39) of primary DNA pools, prepared from high-density grids each containing around 300–400 YAC clones. Primary pools are screened by PCR to identify a pool which contains a positive clone. A secondary PCR screen is then performed on the appropriate set of eight row and 12 column pools, as described by Bentley et al. (1992). PCR primers based on the FA-A cDNA sequence are used as a sequence tagged site (STS) for the 3' region of the gene. The yeast DNA is then amplified with these primers by PCR for 30 cycles of 94° C. for 1 minute, 60° C. for 1 minute and 72° C. for 1 minute, with a final 5 minute extension at 72° C. Confirmation that positive YAC clones contain the majority of the coding sequence of the FA-A genomic gene is obtained by amplification of an STS from the 5' end of the cDNA.

Exon boundaries of the FA-A gene are then characterized e.g. by the vectorette PCR method. This strategy has been described in detail previously (Roberts et al., 1992). With the sequences of the FA-A cDNA and FA-A gene to hand primers derived from these sequences may be used in diagnostic tests to determine the presence of mutations in any part of the genomic FA-A gene of a patient. Such primers will be oligonucleotides comprising a fragment of sequence from the FA-A gene (either intron sequence, exon sequence or a sequence spanning an intron-exon boundary) and will preferably be at least 15 nucleotides in length. More preferably, such primers will be of at least 20 nucleotides in length. Furthermore, with the provision of the FA-A intron sequence information the analysis of a large and as yet untapped source of patient material for mutations will now be possible using methods such as chemical cleavage of mismatches (Cotton et al., 1988; Montandon et al., 1989 which references are herein incorporated by reference) and single-strand conformational polymorphism analysis (Orita et al., 1989, herein incorporated by reference). The efficiency of these methods will permit an alternative method of classification of FA patients by classical complementation analysis. These molecular-genetic methods will likely provide a more rapid method of diagnosis than complementation tests.

Additional experiments may now be performed to identify and characterize regulatory elements flanking the FA-A gene. These regulatory elements may be characterized by standard techniques including deletion analyses wherein successive nucleotides of a putative regulatory region are removed and the effect of the deletions are studied by either transient or long-term expression analyses experiments. The identification and characterization of regulatory elements flanking the genomic FA-A gene may be made by functional experimentation (deletion analyses, etc.) in mammalian cells by either transient or long-term expression analyses.

Having provided a genomic clone for the FA-A gene, it will be apparent to one skilled in the art that either the genomic clone or the cDNA or sequences derived from these clones may be utilized in applications of this invention, including but not limited to, studies of the expression of the FA-A gene, studies of the function of the FA-A protein, the generation of antibodies to the FA-A protein diagnosis of FA-A sufferers and carriers and therapy of FA-A. Descriptions of applications describing the use of FA-A cDNA are therefore intended to comprehend the use of the genomic FA-A gene. It will also be apparent to one skilled in the art that homologs of this gene may now be cloned from other species, such as the mouse, by standard cloning methods. Such homologs will be useful in the production of animal models of Fanconi Anemia.

The following examples are illustrative of the scope of the present invention.

EXAMPLE 1

Determination of Complementation Group

The provision herein of a cDNA clone corresponding to the FA-A gene now enables for the first time a method for determining if FA sufferers have FA attributable specifically to FA complementation group A. Essentially, lymphoblasts derived from patients are transfected with the FA-A cDNA, and the sensitivity of the transfected cells to the DNA cross-linking agents DEB and MMC is determined as described above. A decreased sensitivity of the cells to these agents relative to untransfected lymphocytes from the same patient indicates that the FA mutation of the patient is attributable specifically to FA complementation group A. If the sensitivity of the transfected lymphocytes is unaltered relative to the non-transfected control lymphocytes, then the patient is diagnosed as suffering from FA attributable to a complementation group other than group A.

EXAMPLE 2

Figure 3:
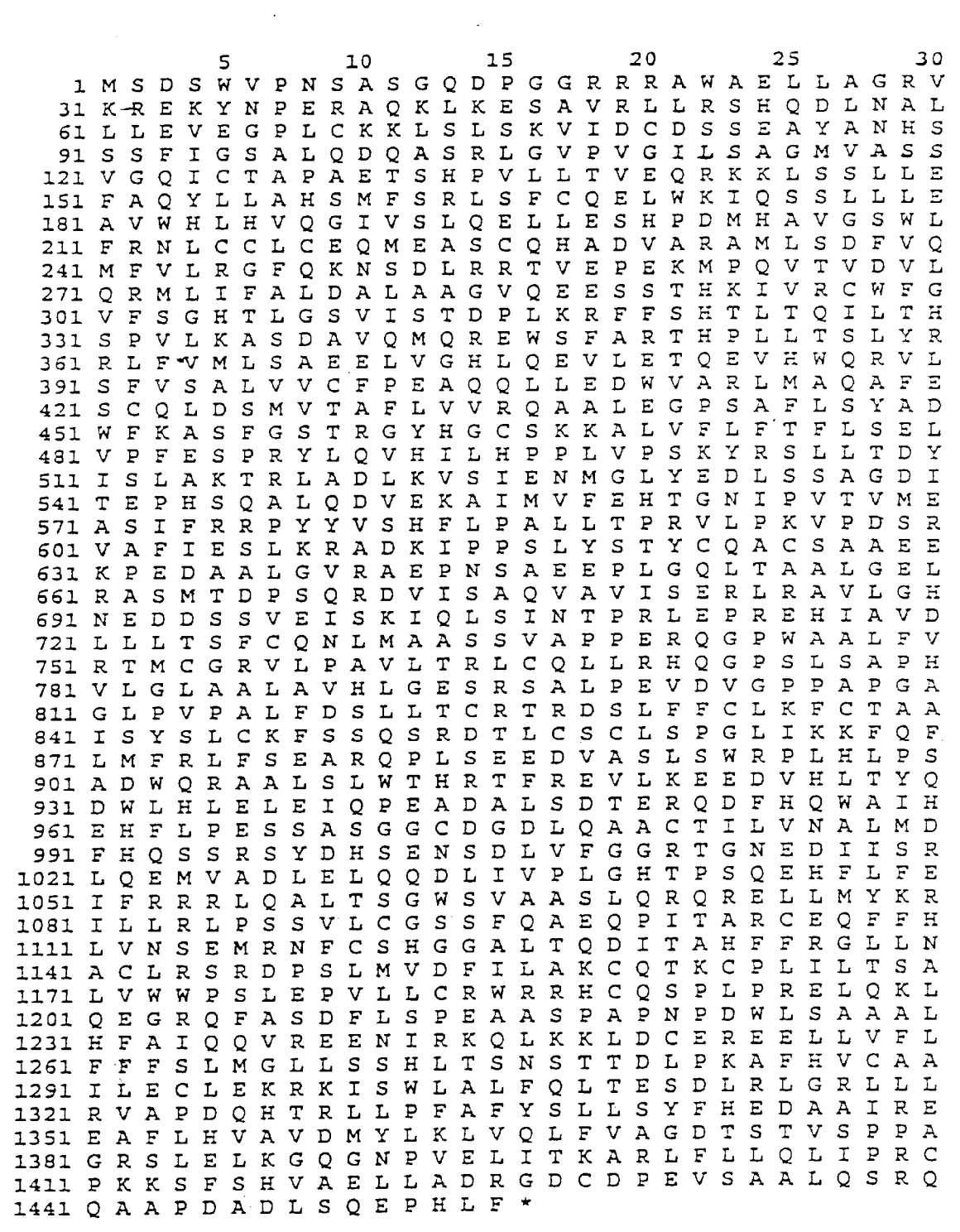

Nucleotide Sequence Variants of FA-A cDNA and Amino Acid Sequence Variants of FA-A Protein FIGS. 2 and 3 show the nucleotide sequence of the FA-A cDNA and the amino acid sequence of the FA-A protein which is encoded by these cDNAs, respectively. It is concluded that the functional characteristic of the FA-A protein is its ability to complement the hypersensitivity of FA-A cells to DNA cross-linking agents, such as MMC. Having presented the nucleotide sequence of the FA-A cDNA and the amino acid sequence of the protein, this invention now also facilitates the creation of DNA molecules, and thereby proteins, which are derived from those disclosed but which vary in their precise nucleotide or amino acid sequence from those disclosed. Such variants may be obtained through a combination of standard molecular biology laboratory techniques and the nucleotide sequence information disclosed by this invention.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the FA-A protein are comprehended by this invention. Also within the scope of this invention are small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of the FA-A cDNA molecule or the FA-A gene and, for the purposes of PCR, will comprise at least a 10–15 nucleotide sequence and, more preferably, a 15–30 nucleotide sequence of the FA-A cDNA or the FA-A gene. DNA molecules and nucleotide sequences which are derived from the disclosed DNA molecules as described above may also be defined as DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a DNA molecule (for example, a deviation of the FA-A cDNA) to a target DNA molecule (for example, the FA-A cDNA) which has been electrophoresed in an agarose gel and transferred to a nitrocellulose membrane by Southern blotting (Southern, 1975), a technique well known in the art and described in (Sambrook et al., 1989). Hybridization with a target probe labeled with [$^{32}$P]-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to $10^9$ CPM/µg or greater). Following hybridization, the nitrocellulose filter is washed to remove back ground hybridization The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$$T_m = 81.5° C. - 16.6(\log_{10}[Na^+]) + 0.41(\%G+C) - 0.63(\%formamide) - (600/l)$$

Where l=the length of the hybrid in base pairs. This equation is valid for concentrations of $Na^+$ in the range of 0.01 M to 0.4 M, and it is less accurate for calculations of $T_m$ in solutions of higher [$Na^+$]. The equation is also primarily valid for DNAs whose G+C content is in the range of 30% is to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe derived the open reading frame of the FA-A cDNA (with a hypothetical % GC=45%), a calculation of hybridization conditions required to give particular stringencies may be made as follows:

For this example, it is assumed that the filter will be washed in 0.3×SSC solution following hybridization, thereby

[$Na^+$]=0.045M

% GC=45%

Formamide concentration=0 l=150 base pairs $T_m = 81.5 - 16(\log_{10}[Na^+]) + (0.41 \times 45) - (600/150)$ and so $T_m = 74.4°$ C.

The $T_m$ of double-stranded DNA decreases by 1–1.5° C. with every 1% decrease in homology (Bonner et al., 1973). Therefore, for this given example, washing the filter in 0.3×SSC at 59.4–64.4° C. will produce a stringency of hybridization equivalent to 90%; that is, DNA molecules with more than 10% sequence variation relative to the target FA-A cDNA will not hybridize. Alternatively, washing the hybridized filter in 0.3×SSC at a temperature of 65.4–68.40° C. will yield a hybridization stringency of 94%; that is, DNA molecules with more than 6% sequence variation relative to the target FA-A cDNA molecule will not hybridize. The above example is given entirely by way of theoretical illustration. One skilled in the art will appreciate that other hybridization techniques may be utilized and that variations in experimental conditions will necessitate alternative calculations for stringency.

In preferred embodiments of the present invention, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. In a most preferred embodiment, stringent conditions are those under which DNA sequences with more than 6% mismatch will not hybridize.

The degeneracy of the genetic code further widens the scope of the present invention as it enables major variations in the nucleotide sequence of a DNA molecule while maintaining the amino acid sequence of the encoded protein. For example, the tenth amino acid residue of the FA-A protein is alanine. This is encoded in the FA-A cDNA by the nucleotide codon triplet GCC. Because of the degeneracy of the genetic code, three other nucleotide codon triplets—GCT, GCG and GCA—also code for alanine. Thus, the nucleotide sequence of the FA-A cDNA could be changed at this position to any of these three codons without affecting the amino acid composition of the encoded protein or the characteristics of the protein. The genetic code and variations in nucleotide codons for particular amino acids is presented in Tables 2 and 3. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein also comprehended by this invention.

TABLE 2

The Genetic Code

| First Position (5' end) | Second Position | | | | Third Position (3' end) |
|---|---|---|---|---|---|
| | T | C | A | G | |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ocre termination triplet, and "Stop (amb)" for the amber. ATG is the most common initiator codon; GTG usually codes for valine, but it can also code for methionine to initiate an mRNA chain.

TABLE 3

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

One skilled in the art will recognize that the DNA mutagenesis techniques described above may be used not only to produce variant DNA molecules, but will also facilitate the production of proteins which differ in certain structural aspects from the FA-A protein, yet which proteins are clearly derivative of this protein and which maintain the essential characteristics of the FA-A protein. Newly derived proteins may also be selected in order to obtain variations on the characteristic of the FA-A protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure (EP 75,444A).

Substitutional variants are those in which at least one residue in the amino acid sequence has been removed and a different residue inserted in its place. Such substitutions generally are made in accordance with the following Table 4 when it is desired to finely modulate the characteristics of the protein. Table 4 shows amino acids which may be substituted for an original amino acid in a protein and which are regarded as conservative substitutions.

TABLE 4

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological dentity are made by selecting substitutions that are less conservative than those in Table 4, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the FA-A protein by analyzing the ability of the derivative proteins to complement the sensitivity to DNA cross-linking agents exhibited by FA-A cells. These assays may be performed by transfecting DNA molecules encoding the derivative proteins into FA-A cells as described above.

The FA-A gene, FA-A cDNA, DNA molecules derived therefrom and the protein encoded by the cDNA and derivative DNA molecules may be utilized in aspects of both the study of FA and for diagnostic and therapeutic applications related to FA. Utilities of the present invention include, but are not limited to, those utilities described in the examples presented herein. Those skilled in the art will recognize that the utilities herein described are not limited to the specific experimental modes and materials presented and will appreciate the wider potential utility of this invention.

EXAMPLE 3

Expression of FA-A cDNA Sequences

With the provision of the FA-A cDNA, the expression and purification of the FA-A protein by standard laboratory techniques is now enabled. The purified protein may be used for function analyses, antibody production and patient therapy. Furthermore, the DNA sequence of the FA-A cDNA can be manipulated in studies to understand the expression of the gene and the function of its product. In this way, the underlying biochemical defect which results in the symptoms of FA-A can be established. Mutant forms of the FA-A isolated to date and others which may be isolated based upon information contained herein, may be studied in order to detect alteration in expression patterns in terms of relative quantities, tissue specificity and functional properties of the encoded mutant FA-A protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacz or trpE gene linked to FA-A proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coli* in large amounts for functional studies. Methods and plasmid vectors for producing fusion proteins and intact native proteins in bacteria are described in Sambrook et al. (1989) (ch. 17, herein incorporated by reference). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (1989) and are well known in the art. Often, proteins expressed at high levels are found in insoluble inclusion bodies. Methods for extracting proteins from these aggregates are described by Sambrook et al. (1989) (ch. 17). Vector systems suitable for the expression of lacZ fusion genes include the pUR series of vectors (Ruther and Muller-Hill, 1983), pEX1-3 (Stanley and Luzio, 1984) and pMR100 (Gray et al., 1982). Vectors suitable for the production of intact native proteins include pKC30 (Shimatake and Rosenberg, 1981), pKK177-3 (Amann and Brosius, 1985) and pET-3 (Studiar and Moffatt, 1986). FA-A fusion proteins may be isolated from protein gels, lyophilized, ground into a powder and used as an antigen. The DNA sequence can also be transferred from its existing context in pREP4 to other cloning vehicles, such as other plasmids, bacteriophages, cosmids, animal viruses and yeast artificial chromosomes (YACs) (Burke et al., 1987). These vectors may then be introduced into a variety of hosts including somatic cells, and simple or complex organisms, such as bacteria, fungi (Timberlake and Marshall, 1989), invertebrates, plants (Gasser and Fraley, 1989), and pigs (Pursel et al., 1989), which cell or organisms are rendered transgenic by the introduction of the heterologous FA-A cDNA.

For expression in mammalian cells, the cDNA sequence may be ligated to heterologous promoters, such as the simian virus (SV)40, promoter in the pSV2 vector (Mulligan and Berg, 1981), and introduced into cells, such as monkey COS-1 cells (Gluzman, 1981), to achieve transient or long-term expression. The stable integration of the chimeric gene construct may be maintained in mammalian cells by biochemical selection, such as neomycin (Southern and Berg, 1982) and mycophoenolic ? acid (Mulligan and Berg, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) is introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., 1981; Gorman et al., 1982), and indeed the pREP4 vector (Groger et al., 1989) described above is an example of such vectors. The level of expression of the cDNA can be manipulated with this type of vector, either by using promoters that have different activities (for example, the baculovirus pAC373 can express cDNAs at high levels in *S. frugiperda* cells (Summers and Smith, 1985) or by using vectors that contain promoters amenable to modulation, for example, the glucocorticoid-responsive promoter from the mouse mammary tumor virus (Lee et al., 1982). The expression of the cDNA can be monitored in the recipient cells 24 to 72 hours after introduction (transient expression).

In addition, some vectors contain selectable markers such as the gpt (Mulligan and Berg, 1981) or neo (Southern and Berg, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., 1981) or Epstein-Barr (Sugden et al., 1985). Such episomal vectors are exemplified by the pREP4 Epstein-Barr virus vector in which the cDNA library described above was constructed. Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, 1973) or strontium phosphate (Brash et al., 1987), electroporation (Neumann et al., 1982), lipofection (Felgner et al., 1987), DEAE dextran (McCuthan et al., 1968), microinjection (Mueller et al., 1978), protoplast fusion (Schafner, 1980), or pellet guns (Klein et al., 1987). Alternatively, the cDNA can be introduced by infection with virus vectors. Systems are developed that use, for example, retroviruses (Bernstein et al., 1985), adenoviruses (Ahmad et al., 1986), or Herpes virus (Spaete et al., 1982).

These eukaryotic expression systems can be used for studies of the FA-A gene and mutant forms of this gene, the FA-A protein and mutant forms of this protein. Such uses include, for example, the identification of regulatory elements located in the 5' region of the FA-A gene on genomic clones that can be isolated from human genomic DNA libraries using the information contained in the present invention. The eukaryotic expression systems may also be used to study the function of the normal complete protein, specific portions of the protein, or of naturally occurring or artificially produced mutant proteins. Naturally occurring mutant proteins exist in patients with FA, while artificially produced mutant proteins can be designed by site directed mutagenesis as described above. These latter studies may probe the function of any desired amino acid residue in the protein by mutating the nucleotide coding for that amino acid.

Using the above techniques, the expression vectors containing the FA gene sequence or fragments or variants or mutants thereof can be introduced into human cells, mammalian cells from other species or non-mammalian cells as desired. The choice of cell is determined by the purpose of the treatment. For example, monkey COS cells (Gluzman, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts (as described herein) may be used.

The following is provided as one exemplary method to express FA-A polypeptide from the cloned FA-A cDNA sequences in mammalian cells. Cloning vector pXTI, commercially available from Stratagene, contains the Long Terminal Repeats (LTRs) and a portion of the GAG gene from Moloney Murine Leukemia Virus. The position of the viral LTRs allows highly efficient, stable transfection of the region within the LTRs. The vector also contains the Herpes Simplex Thymidine Kinase promoter (TK), active in embryonal cells and in a wide variety of tissues in mice, and a selectable neomycin gene conferring G418 resistance. Two unique restriction sites BglII and XhoI are directly downstream from the TK promoter. FA-A cDNA, including the entire open reading frame for the FA-A protein and the 3' untranslated region of the cDNA is cloned into one of the two unique restriction sites downstream from the promoter.

The ligated product is transfected into mouse NIH 3T3 cells using Lipofectin (Life Technologies, Inc.) under conditions outlined in the product specification. Positive transfectants are selected after growing the transfected cells in 600 $\mu$g/ml G418 (Sigma, St. Louis, Mo.). The protein is released into the supernatant and may be purified by standard immunoaffinity chromatography techniques using antibodies raised against the FA-A protein, as described below.

Expression of the FA-A protein in eukaryotic cells may also be used as a source of proteins to raise antibodies. The FA-A protein may be extracted following release of the protein into the supernatant as described above, or, the cDNA sequence may be incorporated into a eukaryotic expression vector and expressed as a chimeric protein with, for example, $\beta$-globin. Antibody to $\beta$-globin is thereafter used to purify the chimeric protein. Corresponding protease cleavage sites engineered between the $\beta$-globin gene and the cDNA are then used to separate the two polypeptide fragments from one another after translation. One useful expression vector for generating $\beta$-globin chimeric proteins is pSG5 (Stratagene). This vector encodes rabbit $\beta$-globin.

The recombinant cloning vector, according to this invention, then comprises the selected DNA of the DNA sequences of this invention for expression in a suitable host. The DNA is operatively linked in the vector to an expression control sequence in the recombinant DNA molecule so that the FA-A polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of *E. coli*, Pseudomonas, *Bacillus subtilis, Bacillus stearothermophilus* or other bacilli; other bacteria; yeast; fungi; insect; mouse or other animal; or plant hosts; or human tissue cells.

It is appreciated that for mutant or variant DNA sequences, similar systems are employed to express and produce the mutant product.

EXAMPLE 4

Production of an Antibody to FA-A Protein

Monoclonal or polyclonal antibodies may be produced to either the normal FA-A protein or mutant forms of this protein. Optimally, antibodies raised against the FA-A protein would specifically detect the FA-A protein. That is, such antibodies would recognize and bind the FA-A protein and would not substantially recognize or bind to other proteins found in human cells. The determination that an antibody specifically detects the FA-A protein is made by any one of a number of standard immunoassay methods; for instance, the Western blotting technique (Sambrook et al., 1989). To determine that a given antibody preparation (such as one produced in a mouse) specifically detects the FA-A protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the FA-A protein will, by this technique, be shown to bind to the FA-A protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-FA-A protein binding.

Substantially pure FA-A protein suitable for use as an immunogen is isolated from the transfected or transformed cells as described in Example 3 above. Concentration of protein in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion.

Monoclonal antibody to epitopes of the FA-A protein identified and isolated as described can be prepared from murine hybridomas according to the classical method of Kohler and Milstein (1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988).

B. Polyclonal Antibody Production by Immunization.

Polyclonal antiserum containing antibodies to heterogenous epitopes of a single protein can be prepared by immunizing suitable animals with the expressed protein (Example 3), which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher (1980).

C. Antibodies Raised Against Synthetic Peptides.

A third approach to raising antibodies against the FA-A protein is to use synthetic peptides synthesized on a commercially available peptide synthesizer based upon the predicted amino acid sequence of the FA-A protein.

D. Antibodies Raised by Injection of FA-A Gene.

Antibodies may be raised against the FA-A protein by subcutaneous injection of a DNA vector which expresses the FA-A protein into laboratory animals, such as mice. Delivery of the recombinant vector into the animals may be achieved using a hand-held form of the Biolistic system (Sanford et al., 1987) as described by Tang et al. (1992). Expression vectors suitable for this purpose may include those which express the FA-A gene under the transcriptional control of either the human $\beta$-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

EXAMPLE 5

DNA-Based Diagnosis

One major application of the FA-A sequence information presented herein is in the area of genetic testing, carrier detection and prenatal diagnosis for FA-A. The gene sequence of the FA-A gene, including intron-exon boundaries is also useful in such diagnostic methods. Individuals carrying mutations in the FA-A gene (disease carrier or patients) may be detected at the DNA level with the use of a variety of techniques. For such a diagnostic procedure, a biological sample of the subject, which biological sample contains either DNA or RNA derived from the subject, is assayed for the presence of a mutant FA-A gene. Suitable biological samples include samples containing genomic DNA or RNA obtained from body cells, such as those present in peripheral blood, urine, saliva, tissue biopsy, surgical specimen, amniocentesis samples and autopsy material. The detection in the biological sample of either a mutant FA-A gene or a mutant FA-A RNA may be performed by a number of methodologies, as outlined below.

A preferred embodiment of such detection techniques is the polymerase chain reaction amplification of reverse transcribed RNA (RT-PCR) of RNA isolated from lymphocytes followed by direct DNA sequence determination of the products. The presence of one or more nucleotide difference between the obtained sequence and the cDNA sequences, and especially, differences in the ORF portion of the nucleotide sequence are taken as indicative of a potential FA-A gene mutation. The effect of such nucleotide differences may be determined by engineering the nucleotide differences into the FA-A cDNA by transfecting the altered cDNA into FA-A cells. Transfected cells are then examined for their sensitivity to DNA cross-linking agents such as MMC. If the cells show the same sensitivity to those agents as non-FA cells (i.e., the altered cDNA complements the FA-A mutation), then the observed nucleotide differences are regarded as "neutral," and the patient is not classified as an FA-A carrier or sufferer on the basis of this nucleotide difference. On the other hand, if the altered cDNA does not complement the sensitivity of the cells to the mutagenic agents, the nucleotide difference is regarded as a mutation rather than a natural difference, and the patient is classified as an FA-A sufferer or carrier.

Because of the diploid nature of the human genome, both copies of the FA-A gene need to be examined to distinguish between FA-A carriers and FA-A sufferers. If a single copy of the FA-A gene is found to be mutated and the other copy is "normal," then the subject is classified as an FA-A carrier or heterozygote. If both copies of the FA-A gene are found to be mutated and do not complement the MMC hypersensitivity of FA-A cells, then the subject is classified as an FA-A sufferer.

Alternatively, DNA extracted from lymphocytes or other cells may be used directly for amplification. The direct amplification from genomic DNA would be appropriate for analysis of the entire FA-A gene including regulatory sequences located upstream and downstream from the open reading frame. Recent reviews of direct DNA diagnosis have been presented by Caskey (1989) and by Landegren et al. (1989).

Further studies of FA-A genes isolated from FA-A patients may reveal particular mutations which occur at a high frequency within this population of individuals. In this case, rather than sequencing the entire FA-A gene, it may be possible to design DNA diagnostic methods to specifically detect the most common FA-A mutations.

The detection of specific DNA mutations may be achieved by methods such as hybridization using specific oligonucleotides (Wallace et al., 1986), direct DNA sequencing (Church and Gilbert, 1988), the use of restriction enzymes (Flavell et al., 1978; Geever et al., 1981), discrimination on the basis of electrophoretic mobility in gels with denaturing reagent (Myers and Maniatis, 1986), RNase protection (Myers et al., 1985), chemical cleavage (Cotton et al., 1985), and the ligase-mediated detection procedure (Landegren et al., 1988).

Oligonucleotides specific to normal or mutant sequences are chemically synthesized using commercially available machines, labelled radioactively with isotopes (such as $^{32}P$) or non-radioactively (with tags such as biotin (Ward and Langer et al., 1981), and hybridized to individual DNA samples immobilized on membranes or other solid supports by dot-blot or transfer from gels after electrophoresis. The presence or absence of these specific sequences are visualized by methods such as autoradiography or fluorometric (Landegren, et al., 1989) or calorimetric reactions (Gebeyehu et al., 1987).

Sequence differences between normal and mutant forms of that gene may also be revealed by the direct DNA sequencing method of Church and Gilbert (1988). Cloned DNA segments may be used as probes to detect specific DNA segments. The sensitivity of this method is greatly enhanced when combined with PCR (Wrichnik et al., 1987; Wong et al., 1987; Stoflet et al., 1988). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, 1975). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (WO 91/10734; Nagamine et al., 1989). DNA fragments of different sequence compositions may be distinguished on denaturing formamide gradient gels in which the mobilities of different DNA fragments are retarded in the gel at different positions according to their specific "partial-melting" temperatures (Myers et al., 1985). Alternatively, a method of detecting a mutation comprising a single base substitution or other small change could be based on differential primer length in a PCR. For example, an invariant primer could be used in addition to a primer specific for a mutation. The PCR products of the normal and mutant genes can then be differentially detected in acrylamide gels.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., 1989). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify specific individual genotypes.

If more than one mutation is frequently encountered in the FA-A gene, a system capable of detecting such multiple mutations would be desirable. For example, a PCR with multiple, specific oligonucleotide primers and hybridization probes may be used to identify all possible mutations at the same time (Chamberlain et al., 1988). The procedure may involve immobilized sequence-specific oligonucleotides probes (Saiki et al., 1989).

EXAMPLE 6

Quantitation of FA-A Protein

An alternative method of diagnosing FA-A sufferers or FA-A carrier status may be to quantitate the level of FA-A protein in the cells of an individual. This diagnostic tool would be useful for detecting reduced levels of the FA-A protein which result from, for example, mutations in the promoter regions of the FA-A gene or mutations within the coding region of the gene which produced truncated, non-functional polypeptides. The determination of reduced FA-A protein levels would be an alternative or supplemental approach to the direct determination of FA status by nucleotide sequence determination outlined above. The availability of antibodies specific to the FA-A protein would allow the quantitation of cellular FA-A protein by one of a number of immunoassay methods which are well known in the art and are presented in Harlow and Lane (1988).

For the purposes of quantitating the FA-A protein, a biological sample of the subject, which sample includes cellular proteins, is required. Such a biological sample may be obtained from body cells, such as those present in peripheral blood, urine, saliva, tissue biopsy, amniocentesis samples, surgical specimens and autopsy material. Quantitation of FA-A protein would be made by immunoassay and compared to levels of the protein found in non-FA human cells. A significant (preferably 50% or greater) reduction in the amount of FA-A protein in the cells of a subject compared to the amount of FA-A protein found in non-FA human cells would be taken as an indication that the subject may be an FA sufferer or FA carrier.

EXAMPLE 7

Gene Therapy

The death of FA sufferers usually results from one or more conditions arising from hematopoietic failure. Bone marrow transplantation (BMT) may be performed in order to treat this problem; however, the lack of a suitable donor may prevent this course of treatment and conventional BMT is still associated with potentially fatal risks (Ebell et al., 1989), many arising from the risk of transplant rejection and the immunosuppression regimes required to minimize this risk. An improved gene therapy approach to BMT for FA-A patients is now made possible by the present work. Essentially, bone marrow cells may be removed from an FA patient and transfected with an expression vector containing the FA-A cDNA. These transfected bone marrow cells will thereby produce functional FA-A protein and can be reintroduced into the patient without concern of rejection.

The scientific and medical procedures required for this approach—bone marrow transplantation and human cell transfection—are now routine procedures. The provision herein of FA-A cDNAs now allows the development of human gene therapy based upon these procedures. Immunotherapy of melanoma patients using genetically engineered tumor-infiltrating lymphocytes (TILs) has been reported by Rosenberg et al. (1990). In that study, a retrovirus vector was used to introduce a gene for neomycin resistance into TILs. A similar approach may be used to introduce the FA-A cDNA into bone marrow cells of FA-A patients.

Retroviruses have been considered the preferred vector for experiments in gene therapy, with a high efficiency of infection and stable integration and expression (Orkin et al., 1988). The full length FA gene or cDNA can be cloned into a retroviral vector and driven from either its endogenous promoter or from the retroviral LTR (long terminal repeat). Expression of levels of the normal protein as low as 10% of the endogenous mutant protein in FA-A patients would be expected to be beneficial, since this is a recessive disease. Other viral transfection systems may also be utilized for this type of approach, including Adeno-Associated virus (AAV) (McLaughlin et al., 1988), Vaccinia virus (Moss et al., 1987), Bovine Papilloma virus (Rasmussen et al., 1987) or members of the herpesvirus group such as Epstein-Barr virus (Margolskee et al., 1988). Recent developments in gene therapy techniques include the use of RNA-DNA hybrid oligonucleotides, as described by Cole-Strauss, et al. (1996). This technique may allow for site-specific integration of cloned sequences, permitting accurately targetted gene replacement.

Having illustrated and described the principles of isolating the human FA-A cDNA and its corresponding genomic genes, the protein and modes of use of these biological molecules, it should be apparent to one skilled in the art that the invention can be modified in arrangement and detail without departing from such principles. We claim all modifications coming within the spirit and scope of the claims presented herein.

BIBLIOGRAPHY

Ahmad et al. (1986). *J. Virol.* 57:267.
Altschul et al. (1990). *J. Mol. Biol.* 215:403–410.
Amann and Brosius (1985). *Gene* 40:183.
Alt et al. (1978). *J. Biol. Chem.* 253:1357.
Arwert and Kwee (1989). In *Fanconi Anemia: Clinical, Cytogenetic, and Experimental Aspects*, 83–92 Schroeder-Kurth et al. (eds.), Springer-Verlag, Berlin.
Auerbach and Wolman (1978). *Nature* 271:69–70.
Auerbach et al. (1989a). *Blood* 73:391–396.
Auerbach et al. (1989b). In *Fanconi Anemia: Clinical, Cytogenetic and Experimental Aspects*, 71–82 Schroeder-Kurth et al. (eds.), Springer-Verlag, Berlin.
Auerbach et al. (1991). *Cancer Genet. Cytogenet.* 51:1–12.
Ausubel et al. (1987). In *Current Protocols in Molecular Biology*, Greene Publishing Associates and Wiley-Intersciences.
Bairoch (1991). *Nucl. Acids Res.* 19:2241–5.
Belt et al. (1989). *Gene* 84:407–417.
Bentley et al. (1992). *Genomics* 12:534–541.
Berger et al. (1980). *Cancer Genet. Cytogenet.* 2:259–267.
Bernstein et al. (1985). *Gen. Engr'g* 7:235.
Bolton and McCarthy (1962). *Proc. Natl. Acad. Sci. USA* 48:1390.
Bonner et al. (1973). *J. Mol. Biol.* 81:123.
Boyd et al. (1990). *Genetics* 125:813–819.
Bradley et al. (1988). *BioTechnigues* 6:114–116.
Brash et al. (1987). *Mol. Cell Biol.* 7:2013.
Breathnach and Chambon (1981). *Ann. Rev. Biochem.* 50:349–383.
Buchwald et al. (1989). In *Fanconi Anaemia: Clinical, Cytogenetic, and Experimental Aspects* 226–235, Schroeder-Kurth et al. (eds.), Springer-Verlag, Berlin.
Buchwald et al. (1987). *Mutation Res.* 184:153–159.
Buchwald (1995). *Nature Genet.* 11:228–230.
Burke et al. (1987). *Science* 236:806–812.
Caskey (1989). *Science* 236:1223–1228.
Cervenka et al. (1981). *Pediatrics* 67:119–127.
Chamberlain et al. (1988). *Nucl. Acids Res.* 16:1141–1155 (1988).
Church and Gilbert (1988). *Proc. Natl. Acad. Sci. USA* 81:1991–1995.
Cole-Strauss, et al. (1996). *Science* 273:1386–1389.
Cotton et al. (1985). *Proc. Natl. Acad. Sci. USA* 85:4397–4401.
Dallapiccola and Porfirio (1989). In *Fanconi Anaemia: Clinical, Cytogenetic, and Experimental Aspects* 145–158, Schroeder-Kurth et al. (eds.), Springer-Verlag, Berlin.
Dingwall et al. (1991). *Trends Biochem. Sci.* 16:478–481.
Duckworth-Rysiecki et al. (1985). *Somatic. Cell. Mol. Genet.* 11:35–41.
Ebell et al. (1989). In *Fanconi Anaemia: Clinical, Cytogenetic, and Experimental Aspects* 47–59, Schroeder-Kurth et al. (eds.), Springer-Verlag, Berlin.
Eisenberg (1984). *Annu. Rev. Biochem.* 53:595–623.
Engvall (1980). *Enzymol.* 70:419.
Feigner et al. (1987). *Proc. Natl. Acad. Sci USA* 84:7413.
Fisher (1980). *Manual of Clinical Immunology*, ch. 42.
Flavell et al. (1978). *Cell* 15:25.
Friedberg et al. (1995). *DNA Repair and Mutagenesis* 633–685.
Gasser and Fraley (1989). *Science* 244:1293.
Gebeyehu et al. (1987). *Nucleic Acids Res.* 15:4513–4534.
Geever et al. (1981). *Proc. Natl. Acad. Sci USA* 78:5081.
Glade and Broder (1971). In *In Vitro Methods in Cell Mediated Immunity* 561–570, Bloom, B. R. and Glade, P. R. (eds.), Academic Press, New York.
Glanz and Fraser (1982). *J. Med. Genet.* 19:412–416.
Gluckman et al. (1989). In *Fanconi Anaemia: Clinical, Cytogenetic, and Experimental Aspects* 60–68, Schroeder-Kurth et al. (eds.), Springer-Verlag, Berlin.
Gluzman (1981). *Cell* 23:175–182.
Gordon-Smith and Rutherford (1991). *Sem. In Hemat.* 28:104–112.
Gorman et al. (1982). *Proc. Natl. Acad. Sci USA* 78:6777–6781.
Graham and vander Eb (1973). *Virology* 52:466.
Gray et al. (1982). *Proc. Natl. Acad. Sci. USA* 79:6598.
Green et al. (1989). *EMBO J.* 8:1067–1072.
Groger et al. (1989). *Gene* 81:285–294.
Harlow and Lane (1988). *Antibodies, A Laboratory Manual*, Cold Spring Harbor Laboratory, New York.
Harnden and Klinger (1985). *An International System for Human Cytogenetic Nomenclature*, published in collaboration with Cytogenetics and Cell Genetics, Karger, Basel.

Harper and Saunders (1981). *Chromosoma* 83:431–439.
Hogervorst (1995). *Nature Genet.* 10:208–212.
Hurst (1994). *Prot. Profile* 1:123–168.
Ishida et al. (1982). *Cancer Res.* 42:4000–4006.
Innis et al. (1990). *PCR Protocols, A Guide to Methods and Applications*, Innis et al. (eds.), Academic Press, Inc., San Diego, Calif.
Jaspers et al. (1988). *Cytogenet. Cell Genet.* 49:259–263.
Joenje (1996). *Hum. Genet.* 97:280–282.
Joenje et al. (1995). *Blood* 86:2156–2160.
Kawasaki et al. (1990). In *PCR Protocols, A Guide to Methods and Applications*, Innis et al. (eds.), 21–27, Academic Press, Inc., San Diego, Calif.
Klein et al. (1987). *Nature* 327:70.
Kneller et al. (1990). *J. Mol. Biol.* 214:171–182.
Kohler and Milstein (1975). *Nature* 256:495.
Kozak (1987). *Nucleic Acids Res.* 15:8125–8148.
Kriegler (1990). In *Gene Transfer and Expression*, 131–132, Stockton Press, New York.
Kruyt et al. (1996). *Blood* 87:938–948.
Landegren et al. (1989). *Science* 242:229–237.
Landegren et al. (1988). *Science* 241:1077.
Lee et al. (1982). *Nature* 294:228.
Leeder et al. (1989). *Anal. Biochem.* 177:364–372.
Lin et al. (1985). *Cytogenet. Cell Genet.* 39:269–274.
Liu et al. (1992). *Am. J. Hum. Genet.* 51:A55.
Liu et al. (1994). *Blood* 84:3995–4007.
Mann et al. (1991). *Genomics* 9:329–337.
Margolskee et al. (1988). *Mol. Cell. Biol.* 8:2837–2847.
McCabe (1990). In *PCR Protocols, A Guide to Methods and Applications*, Innis et al. (eds.), 76–83, Academic Press, New York.
McCuthan et al. (1968). *J. Natl Cancer Inst.* 41:351.
McIntosh et al. (1979). *Am. J. Pediatr. Hematol. Oncol.* 1:107–110.
McLaughlin et al. (1988). *J. Virol.* 62:1963.
Monaco and Lehrach (1991). *Proc. Natl. Acad. Sci. U.S.A.* 88:4123–4127.
Montandon et al. (1989). *Nucleic Acids Res.* 9:3347–3358.
Moss et al. (1987). *Annu. Rev. Immunol.* 5:305.
Moustacchi et al. (1987). *Hum. Genet.* 75:45–47.
Mueller et al. (1978). *Cell* 15:579.
Mulligan and Berg (1981). *Proc. Natl. Acad. Sci. USA* 78:2072–2076.
Mulligan et al. (1981). *Proc. Natl. Acad. Sci. USA* 78:1078–2076.
Myers and Maniatis (1986). *Cold Spring Harbor Symp. Quant. Biol.* 51:275–284.
Myers et al. (1985). *Science* 230:1242.
Nagamine et al. (1989). *Am. J. Hum. Genet.* 45:337–339.
Nakamura et al. (1987). *Science* 235:1616–1622.
Neumann et al. (1982). *EMBO J* 1:841.
Orita et al. (1989). *Genomics* 5:874–879.
Orkin et al. (1988). *Prog. Med. Genet.* 7:130.
Ouchterlony et al. (1973). In *Handbook of Experimental Immunology*, Wier, D. (ed.) chapter 19. Blackwell.
Petridon and Barrett (1990). *Acta Pardiatr. Scand.* 79:1069–1074.
Pronk et al. (1995). *Nature Genet.* 11:338–340.
Proudfoot (1991). *Cell* 64:671–674.
Pursel et al. (1989). *Science* 244:1281–1288.
Rasmussen et al. (1987). *Methods Enzymol.* 139:642.
Riley et al. (1990). *Nucleic Acids Res.* 18:2887–2890.
Roberts et al. (1992). *Genomics* 13:942–950.
Rosenberg et al. (1990). *N. Engl. J. Med.* 323:570–578.
Rousset et al. (1990). *Cancer Res.* 50:2443–2448.
Ruther and Muller-Hill (1983). *EMBO J.* 2:1791.
Saiki et al. (1989). *Proc. Nat. Acad. Sci. USA* 86:6230–6234.
Sambrook et al. (1989). In *Molecular Cloning: A Laboratory Manual*, Cold Spring Harbor, N.Y.
Sanford et al. (1987). *Particulate Sci. Technol.* 5:27–37.
Sanger et al. (1977). *Proc. Natl. Acad. Sci. U.S.A.* 74:5463.
Santerre et al. (1984). *Gene* 30:147–156.
Sarver et al. (1981). *Mol. Cell Biol.* 1:486.
Schafner (1980). *Proc. Natl. Acad. Sci. USA* 77:2163–2167.
Schroeder et al. (1976). *Hum. Genet.* 32:257–288.
Schroeder et al. (1964). *Hum. Genet.* 1:194–196.
Sedivy and Joyner (1992). In *Gene Targeting*, W. H. Freeman and Company, New York.
Shapiro and Senapathy (1987). *Nucleic Acids Res.* 15:7155–7174.
Shimatake and Rosenberg (1981). *Nature* (London) 292:128.
Southern (1975). *J. Mol. Biol.* 98:503.
Southern and Berg (1982). *J. Mol. Appl. Genet.* 1:327–341.
Spaete et al. (1982). *Cell* 30:295.
Stanley and Luzio (1984). *EMBO J.* 3:1429.
Stanners et al. (1971). *Nature New Biology* 230:52–54.
Stoflet et al. (1988). *Science* 239:491–494.
Strathdee et al. (1992a). *Nature Genetics* 1:196–198.
Strathdee et al. (1992b). *Nature* 356:763–767.
Studiar and Moffatt (1986). *J. Mol. Biol.* 189:113.
Sugden et al. (1985). *Mol. Cell Biol.* 5:410.
Summers and Smith (1985). In *Genetically Altered Viruses and the Environment*, Fields et al. (Eds.) 22:319–328, Cold Spring Harbor Laboratory Press, Cold Spring Harbor, N.Y.
Swift (1971). *Nature* 230:370–373.
Szybalski and Iyer (1967). In *Antibiotics, Vol. I. Mechanisms of Action* 211–245, Springer-Verlag, New York.
Tanaka et al. (1989). *Proc. Natl. Acad. Sci. USA* 86:5512–5516.
Tang et al. (1992). *Nature* (London) 356:152–154.
Timberlake and Marshall (1989). *Science* 244:1313–1317.
Trezise and Buchwald (1991). *Nature* 353:434–437.
Tsui and Estevill (1991). In *Genes and Phenotypes* 1–36, Cold Spring Harbor Laboratory Press, Cold Spring Harbor, N.Y.
Vaitukaitis et al. (1971). *J. Clin. Endocrinol. Metab.* 33:988–991.
Van Duuren (1969). *Ann. N.Y. Acad. Sci.* 163:633–651.
Veres et al. (1987). *Science* 237:415–417.
Vermeulen et al. (1991). *Mutation Res.* 255:201–208.
Wallace et al. (1986). *Cold Spring Harbor Symp. Quant. Biol.* 51:257–261.
Ward and Langer et al. (1981). *Proc. Natl. Acad. Sci. USA* 78:6633–6657.
Whitney et al. (1995). *Nature Genetics* 11:341–343.
Winship, P. R. (1989). *Nucleic Acids Res.* 17:1266.
Wong et al. (1987). *Nature* 330:384–386.
Wrichnik et al. (1987). *Nucleic Acids Res.* 15:529–542.
Yamashita et al. (1994). *Proc. Natl. Acad. Sci.* 91:6712–6716.
Youssoufian (1994). *Proc. Natl. Acad. Sci.* 91:7975–7979.

We claim:

1. An isolated nucleic acid molecule encoding a protein comprising an amino acid sequence selected from the group consisting of:
   (a) the sequence set forth in SEQ ID NO: 2; and
   (b) sequences that differ from the sequence set forth in SEQ ID NO: 2 by one or more conservative substitutions,
   and wherein expression of the nucleic acid molecule in FA-A cells complements the hypersensitivity of the cells to mitomycin C.

2. The isolated nucleic acid molecule according to claim 1 wherein the nucleic acid molecule comprises a DNA sequence as set forth in Seq. I.D. No. 1.

3. A recombinant expression vector comprising a nucleic acid sequence according to claim 1.

4. An isolated cell containing the recombinant expression vector of claim 2.

5. An isolated nucleic acid molecule that hybridizes with a nucleic acid probe comprising the open reading frame of SEQ ID NO: 1 under wash conditions of 0.3×SSC at 59.4–64.4° C., and wherein expression of the nucleic acid molecule in FA-A cells complements the hypersensitivity of the cells to mitomycin C.

6. A recombinant expression vector comprising a nucleic acid molecule of claim 5.

7. An isolated cell comprising the recombinant expression vector of claim 6.

8. A method of complementing a genetic defect in a cell in vitro, the defect being a mutation in the Fanconi Anemia gene of complementation group A, the method comprising introducing into the cell a nucleic acid molecule according to claim 1 and expressing the nucleic acid, wherein expression of the nucleic acid complements mitomycin C sensitivity of the cell.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
       (A) LENGTH: 5503
       (B) TYPE: nucleic acid
       (C) STRANDEDNESS: double
       (D) TOPOLOGY: linear (ii) MOLECULE TYPE: cDNA to mRNA (vi) ORIGINAL SOURCE:
       (A) ORGANISM: Homo sapiens (xi) SEQUENCE DESCRIPTION: SEQ ID NO:1:

```
AGCCGCCGC CGGGGCTGTA GGCGCCAAGG CCATGTCCGA CTCGTGGGTC CCGAACTCCG     59
CCTCGGGCCA GGACCCAGGG GGCCGCCGGA GGGCCTGGGC CGAGCTGCTG GCGGGAAGGG   119
TCAAGAGGGA AAAATATAAT CCTGAAAGGG CACAGAAATT AAAGGAATCA GCTGTGCGCC   179
TCCTGCGAAG CCATCAGGAC CTGAATGCCC TTTTGCTTGA GGTAGAAGGT CCACTGTGTA   239
AAAAATTGTC TCTCAGCAAA GTGATTGACT GTGACAGTTC TGAGGCCTAT GCTAATCATT   299
CTAGTTCATT TATAGGCTCT GCTTTGCAGG ATCAAGCCTC AAGGCTGGGG GTTCCCGTGG   359
GTATTCTCTC AGCCGGGATG GTTGCCTCTA GCGTGGGACA GATCTGCACG GCTCCAGCGG   419
AGACCAGTCA CCCTGTGCTG CTGACTGTGG AGCAGAGAAA GAAGCTGTCT TCCCTGTTAG   479
AGTTTGCTCA GTATTTATTG GCACACAGTA TGTTCTCCCG TCTTTCCTTC TGTCAAGAAT   539
TATGGAAAAT ACAGAGTTCT TTGTTGCTTG AAGCGGTGTG GCATCTTCAC GTACAAGGCA   599
TTGTGAGCCT GCAAGAGCTG CTGGAAAGCC ATCCCGACAT GCATGCTGTG GGATCGTGGC   659
TCTTCAGGAA TCTGTGCTGC CTTTGTGAAC AGATGGAAGC ATCCTGCCAG CATGCTGACG   719
TCGCCAGGGC CATGCTTTCT GATTTTGTTC AAATGTTTGT TTTGAGGGGA TTTCAGAAAA   779
ACTCAGATCT GAGAAGAACT GTGGAGCCTG AAAAAATGCC GCAGGTCACG GTTGATGTAC   839
TGCAGAGAAT GCTGATTTTT GCACTTGACG CTTTGGCTGC TGGAGTACAG GAGGAGTCCT   899
CCACTCACAA GATCGTGAGG TGCTGGTTCG GAGTGTTCAG TGGACACACG CTTGGCAGTG   959
TAATTTCCAC AGATCCTCTG AAGAGGTTCT TCAGTCATAC CCTGACTCAG ATACTCACTC  1019
ACAGCCCTGT GCTGAAAGCA TCTGATGCTG TTCAGATGCA GAGAGAGTGG AGCTTTGCGC  1079
GGACACACCC TCTGCTCACC TCACTGTACC GCAGGCTCTT TGTGATGCTG AGTGCAGAGG  1139
AGTTGGTTGG CCATTTGCAA GAAGTTCTGG AAACGCAGGA GGTTCACTGG CAGAGAGTGC  1199
TCTCCTTTGT GTCTGCCCTG GTTGTCTGCT TCCAGAAGC GCAGCAGCTG CTTGAAGACT  1259
GGGTGGCGCG TTTGATGGCC CAGGCATTCG AGAGCTGCCA GCTGGACAGC ATGGTCACTG  1319
CGTTCCTGGT TGTGCGCCAG GCAGCACTGG AGGGCCCCTC TGCGTTCCTG TCATATGCAG  1379
ACTGGTTCAA GGCCTCCTTT GGGAGCACAC GAGGCTACCA TGGCTGCAGC AAGAAGGCCC  1439
TGGTCTTCCT GTTTACGTTC TTGTCAGAAC TCGTGCCTTT TGAGTCTCCC CGGTACCTGC  1499
AGGTGCACAT TCTCCACCCA CCCCTGGTTC CCAGCAAGTA CCGCTCCCTC CTCACAGACT  1559
ACATCTCATT GGCCAAGACA CGGCTGGCCG ACCTCAAGGT TTCTATAGAA AACATGGGAC  1619
TCTACGAGGA TTTGTCATCA GCTGGGGACA TTACTGAGCC CCACAGCCAA GCTCTTCAGG  1679
ATGTTGAAAA GGCCATCATG GTGTTTGAGC ATACGGGGAA CATCCCAGTC ACCGTCATGG  1739
```

```
AGGCCAGCAT ATTCAGGAGG CCTTACTACG TGTCCCACTT CCTCCCCGCC CTGCTCACAC    1799

CTCGAGTGCT CCCCAAAGTC CCTGACTCCC GTGTGGCGTT TATAGAGTCT CTGAAGAGAG    1859

CAGATAAAAT CCCCCCATCT CTGTACTCCA CCTACTGCCA GGCCTGCTCT GCTGCTGAAG    1919

AGAAGCCAGA AGATGCAGCC CTGGGAGTGA GGGCAGAACC CAACTCTGCT GAGGAGCCCC    1979

TGGGACAGCT CACAGCTGCA CTGGGAGAGC TGAGAGCCTC CATGACAGAC CCCAGCCAGC    2039

GTGATGTTAT ATCGGCACAG GTGGCAGTGA TTTCTGAAAG ACTGAGGGCT GTCCTGGGCC    2099

ACAATGAGGA TGACAGCAGC GTTGAGATAT CAAAGATTCA GCTCAGCATC AACACGCCGA    2159

GACTGGAGCC ACGGGAACAC ATTGCTGTGG ACCTCCTGCT GACGTCTTTC TGTCAGAACC    2219

TGATGGCTGC CTCCAGTGTC GCTCCCCCGG AGAGGCAGGG TCCCTGGGCT GCCCTCTTCG    2279

TGAGGACCAT GTGTGGACGT GTGCTCCCTG CAGTGCTCAC CCGGCTCTGC CAGCTGCTCC    2339

GTCACCAGGG CCCGAGCCTG AGTGCCCCAC ATGTGCTGGG GTTGGCTGCC CTGGCCGTGC    2399

ACCTGGGTGA GTCCAGGTCT GCGCTCCCAG AGGTGGATGT GGGTCCTCCT GCACCTGGTG    2459

CTGGCCTTCC TGTCCCTGCG CTCTTTGACA GCCTCCTGAC CTGTAGGACG AGGGATTCCT    2519

TGTTCTTCTG CCTGAAATTT TGTACAGCAG CAATTTCTTA CTCTCTCTGC AAGTTTTCTT    2579

CCCAGTCACG AGATACTTTG TGCAGCTGCT TATCTCCAGG CCTTATTAAA AAGTTTCAGT    2639

TCCTCATGTT CAGATTGTTC TCAGAGGCCC GACAGCCTCT TTCTGAGGAG GACGTAGCCA    2699

GCCTTTCCTG GAGACCCTTG CACCTTCCTT CTGCAGACTG GCAGAGAGCT GCCCTCTCTC    2759

TCTGGACACA CAGAACCTTC CGAGAGGTGT TGAAAGAGGA AGATGTTCAC TTAACTTACC    2819

AAGACTGGTT ACACCTGGAG CTGGAAATTC AACCTGAAGC TGATGCTCTT TCAGATACTG    2879

AACGGCAGGA CTTCCACCAG TGGGCGATCC ATGAGCACTT TCTCCCTGAG TCCTCGGCTT    2939

CAGGGGGCTG TGACGGAGAC CTGCAGGCTG CGTGTACCAT TCTTGTCAAC GCACTGATGG    2999

ATTTCCACCA AAGCTCAAGG AGTTATGACC ACTCAGAAAA TTCTGATTTG GTCTTTGGTG    3059

GCCGCACAGG AAATGAGGAT ATTATTTCCA GATTGCAGGA GATGGTAGCT GACCTGGAGC    3119

TGCAGCAAGA CCTCATAGTG CCTCTCGGCC ACACCCCTTC CCAGGAGCAC TTCCTCTTTG    3179

AGATTTTCCG CAGACGGCTC CAGGCTCTGA CAAGCGGGTG GAGCGTGGCT GCCAGCCTTC    3239

AGAGACAGAG GGAGCTGCTA ATGTACAAAC GGATCCTCCT CCGCCTGCCT TCGTCTGTCC    3299

TCTGCGGCAG CAGCTTCCAG GCAGAACAGC CCATCACTGC CAGATGCGAG CAGTTCTTCC    3359

ACTTGGTCAA CTCTGAGATG AGAAACTTCT GCTCCCACGG AGGTGCCCTG ACACAGGACA    3419

TCACTGCCCA CTTCTTCAGG GGCCTCCTGA ACGCCTGTCT GCGGAGCAGA GACCCCTCCC    3479

TGATGGTCGA CTTCATACTG GCCAAGTGCC AGACGAAATG CCCCTTAATT TTGACCTCTG    3539

CTCTGGTGTG GTGGCCGAGC CTGGAGCCTG TGCTGCTCTG CCGGTGGAGG AGACACTGCC    3599

AGAGCCCGCT GCCCCGGGAA CTGCAGAAGC TACAAGAAGG CCGGCAGTTT GCCAGCGATT    3659

TCCTCTCCCC TGAGGCTGCC TCCCCAGCAC CCAACCCGGA CTGGCTCTCA GCTGCTGCAC    3719

TGCACTTTGC GATTCAACAA GTCAGGGAAG AAAACATCAG GAAGCAGCTA AGAAGCTGG    3779

ACTGCGAGAG AGAGGAGCTA TTGGTTTTCC TTTTCTTCTT CTCCTTGATG GGCCTGCTGT    3839

CGTCACATCT GACCTCAAAT AGCACCACAG ACCTGCCAAA GGCTTTCCAC GTTTGTGCAG    3899

CAATCCTCGA GTGTTTAGAG AAGAGGAAGA TATCCTGGCT GGCACTCTTT CAGTTGACAG    3959

AGAGTGACCT CAGGCTGGGG CGGCTCCTCC TCCGTGTGGC CCCGGATCAG CACACCAGGC    4019

TGCTGCCTTT CGCTTTTTAC AGTCTTCTCT CCTACTTCCA TGAAGACGCG GCCATCAGGG    4079

AAGAGGCCTT CCTGCATGTT GCTGTGGACA TGTACTTGAA GCTGGTCCAG CTCTTCGTGG    4139
```

-continued

```
CTGGGGATAC AAGCACAGTT TCACCTCCAG CTGGCAGGAG CCTGGAGCTC AAGGGTCAGG    4199

GCAACCCCGT GGAACTGATA ACAAAAGCTC GTCTTTTTCT GCTGCAGTTA ATACCTCGGT    4259

GCCCGAAAAA GAGCTTCTCA CACGTGGCAG AGCTGCTGGC TGATCGTGGG GACTGCGACC    4319

CAGAGGTGAG CGCCGCCCTC CAGAGCAGAC AGCAGGCTGC CCCTGACGCT GACCTGTCCC    4379

AGGAGCCTCA TCTCTTCTGA CGGGACCTGC CACTGCACAC CAGCCCAGCT CCCGTGTAAA    4439

TAATTTATTA CAAGCATAAC ATGGAGCTCT TGTTGCACTA AAAAGTGGAT TACAAATCTC    4499

CTCGACTGCT TTAGTGGGGA AAGGAATCAA TTATTTATGA ACTGTCCGGC CCCGAGTCAC    4559

TCAGCGTTTG CGGGAAAATA AACCACTGGT CCCAGAGCAG AGGAAGGCTA CTTGAGCCGG    4619

ACACCAAGCC CGCCTCCAGC ACCAAGGGCG GGCAGCACCC TCCGACCCTC CCATGCGGGT    4679

GCACACGAAG GGTGAGGCTG ACACAGCCAC TGCGGAGTCC AGGCTGCTAG AGGTGCTCAT    4739

CCTCACTGCC GTCCTCAGGT GGGTTCGGGC TTCACCGCCT GGCCCTCTGT GGTCACAGAG    4799

GGGCTCGGTG GCCCAGGTGG TGGTTCCGCC TCCAGGGGCA GGGCCTTGTC CTGGGTCTGT    4859

GTCAGCGGGT GCACCATGGA CATGTGTACA TTGAGGTTGT GGGCCTTCTC AAACCGCCGG    4919

CCACACTGGT CACAGGCAAA GTCCAGCTCA GTCTCAGCCT TGTGTTTGGT CATGTGGTAC    4979

TTGAGGGATG CCCGCTGCCT GCACTGGAAC CCACAGACCT CACACCTGGG GGACAGAGGC    5039

AGATAAGAAG GTGCGAGGCC ACAGCCCTGG GAGGGGGTCC TGACTCACAC TTACTGCAAA    5099

GGCTTGGCTC CCGAATGTCG CATTTGGTGG ACGAGAAGGT GCTTCCGCTG CTTGAAGGTT    5159

TGTCCACATT CGTCACAGAT ATAGTTCCGC ACCTCTGAGA GGGGAGAGTC CAGTGAGTCC    5219

AGGCCCCTGA TGCTCCAACC TCCCGGGGGG ACGACGATGA CAATGTGAAA CCATCACAGC    5279

TGGGAAGACA TTTCTGCACA TGGTTCACCA TGCAGTGGGC CCAAGCAAGG GGCCTATGAG    5339

GGCCTCGTTT ATTAAGATCT TTAAACTGCT TTATACACTG TCACGTGGCT TCATCAGCTG    5399

TGTGCATTTC AGGATGGTTT TTAAAGAAAC CTCAGAAAGC TATTTCCTTA AAAAAAAAAA    5459

AAAAAAAAAA AAAAAAAAAA AAAAAAAAAA AAAAAAAAAA AAAA                    5503
```

(2) INFORMATION FOR SEQ ID NO:2:

(i) SEQUENCE CHARACTERISTICS:
        (A) LENGTH: 1455
        (B) TYPE: amino acid
        (C) STRANDEDNESS:
        (D) TOPOLOGY: Linear (xi) SEQUENCE DESCRIPTION: SEQ ID NO:2:

```
Met Ser Asp Ser Trp Val Pro Asn Ser Ala Ser Gly Gln Asp Pro
 1               5                  10                  15

Gly Gly Arg Arg Arg Ala Trp Ala Glu Leu Leu Ala Gly Arg Val
                20                  25                  30

Lys Arg Glu Lys Tyr Asn Pro Glu Arg Ala Gln Lys Leu Lys Glu
                35                  40                  45

Ser Ala Val Arg Leu Leu Arg Ser His Gln Asp Leu Asn Ala Leu
                50                  55                  60

Leu Leu Glu Val Glu Gly Pro Leu Cys Lys Lys Leu Ser Leu Ser
                65                  70                  75

Lys Val Ile Asp Cys Asp Ser Glu Ala Tyr Ala Asn His Ser
                80                  85                  90

Ser Ser Phe Ile Gly Ser Ala Leu Gln Asp Gln Ala Ser Arg Leu
                95                  100                 105

Gly Val Pro Val Gly Ile Leu Ser Ala Gly Met Val Ala Ser Ser
```

```
                        110                 115                 120
Val Gly Gln Ile Cys Thr Ala Pro Ala Glu Thr Ser His Pro Val
                125                 130                 135
Leu Leu Thr Val Glu Gln Arg Lys Lys Leu Ser Ser Leu Leu Glu
                140                 145                 150
Phe Ala Gln Tyr Leu Leu Ala His Ser Met Phe Ser Arg Leu Ser
                155                 160                 165
Phe Cys Gln Glu Leu Trp Lys Ile Gln Ser Ser Leu Leu Leu Glu
                170                 175                 180
Ala Val Trp His Leu His Val Gln Gly Ile Val Ser Leu Gln Glu
                185                 190                 195
Leu Leu Glu Ser His Pro Asp Met His Ala Val Gly Ser Trp Leu
                200                 205                 210
Phe Arg Asn Leu Cys Cys Leu Cys Glu Gln Met Glu Ala Ser Cys
                215                 220                 225
Gln His Ala Asp Val Ala Arg Ala Met Leu Ser Asp Phe Val Gln
                230                 235                 240
Met Phe Val Leu Arg Gly Phe Gln Lys Asn Ser Asp Leu Arg Arg
                245                 250                 255
Thr Val Glu Pro Glu Lys Met Pro Gln Val Thr Val Asp Val Leu
                260                 265                 270
Gln Arg Met Leu Ile Phe Ala Leu Asp Ala Leu Ala Ala Gly Val
                275                 280                 285
Gln Glu Glu Ser Ser Thr His Lys Ile Val Arg Cys Trp Phe Gly
                290                 295                 300
Val Phe Ser Gly His Thr Leu Gly Ser Val Ile Ser Thr Asp Pro
                305                 310                 315
Leu Lys Arg Phe Phe Ser His Thr Leu Thr Gln Ile Leu Thr His
                320                 325                 330
Ser Pro Val Leu Lys Ala Ser Asp Ala Val Gln Met Gln Arg Glu
                335                 340                 345
Trp Ser Phe Ala Arg Thr His Pro Leu Leu Thr Ser Leu Tyr Arg
                350                 355                 360
Arg Leu Phe Val Met Leu Ser Ala Glu Glu Leu Val Gly His Leu
                365                 370                 375
Gln Glu Val Leu Glu Thr Gln Glu Val His Trp Gln Arg Val Leu
                380                 385                 390
Ser Phe Val Ser Ala Leu Val Val Cys Phe Pro Glu Ala Gln Gln
                395                 400                 405
Leu Leu Glu Asp Trp Val Ala Arg Leu Met Ala Gln Ala Phe Glu
                410                 415                 420
Ser Cys Gln Leu Asp Ser Met Val Thr Ala Phe Leu Val Val Arg
                425                 430                 435
Gln Ala Ala Leu Glu Gly Pro Ser Ala Phe Leu Ser Tyr Ala Asp
                440                 445                 450
Trp Phe Lys Ala Ser Phe Gly Ser Thr Arg Gly Tyr His Gly Cys
                455                 460                 465
Ser Lys Lys Ala Leu Val Phe Leu Phe Thr Phe Leu Ser Glu Leu
                470                 475                 480
Val Pro Phe Glu Ser Pro Arg Tyr Leu Gln Val His Ile Leu His
                485                 490                 495
Pro Pro Leu Val Pro Ser Lys Tyr Arg Ser Leu Leu Thr Asp Tyr
                500                 505                 510
```

```
Ile Ser Leu Ala Lys Thr Arg Leu Ala Asp Leu Lys Val Ser Ile
            515                 520                 525

Glu Asn Met Gly Leu Tyr Glu Asp Leu Ser Ser Ala Gly Asp Ile
            530                 535                 540

Thr Glu Pro His Ser Gln Ala Leu Gln Asp Val Glu Lys Ala Ile
            545                 550                 555

Met Val Phe Glu His Thr Gly Asn Ile Pro Val Thr Val Met Glu
            560                 565                 570

Ala Ser Ile Phe Arg Arg Pro Tyr Tyr Val Ser His Phe Leu Pro
            575                 580                 585

Ala Leu Leu Thr Pro Arg Val Leu Pro Lys Val Pro Asp Ser Arg
            590                 595                 600

Val Ala Phe Ile Glu Ser Leu Lys Arg Ala Asp Lys Ile Pro Pro
            605                 610                 615

Ser Leu Tyr Ser Thr Tyr Cys Gln Ala Cys Ser Ala Ala Glu Glu
            620                 625                 630

Lys Pro Glu Asp Ala Ala Leu Gly Val Arg Ala Glu Pro Asn Ser
            635                 640                 645

Ala Glu Glu Pro Leu Gly Gln Leu Thr Ala Ala Leu Gly Glu Leu
            650                 655                 660

Arg Ala Ser Met Thr Asp Pro Ser Gln Arg Asp Val Ile Ser Ala
            665                 670                 675

Gln Val Ala Val Ile Ser Glu Arg Leu Arg Ala Val Leu Gly His
            680                 685                 690

Asn Glu Asp Asp Ser Ser Val Glu Ile Ser Lys Ile Gln Leu Ser
            695                 700                 705

Ile Asn Thr Pro Arg Leu Glu Pro Arg Glu His Ile Ala Val Asp
            710                 715                 720

Leu Leu Leu Thr Ser Phe Cys Gln Asn Leu Met Ala Ala Ser Ser
            725                 730                 735

Val Ala Pro Pro Glu Arg Gln Gly Pro Trp Ala Ala Leu Phe Val
            740                 745                 750

Arg Thr Met Cys Gly Arg Val Leu Pro Ala Val Leu Thr Arg Leu
            755                 760                 765

Cys Gln Leu Leu Arg His Gln Gly Pro Ser Leu Ser Ala Pro His
            770                 775                 780

Val Leu Gly Leu Ala Ala Leu Ala Val His Leu Gly Glu Ser Arg
            785                 790                 795

Ser Ala Leu Pro Glu Val Asp Val Gly Pro Pro Ala Pro Gly Ala
            800                 805                 810

Gly Leu Pro Val Pro Ala Leu Phe Asp Ser Leu Leu Thr Cys Arg
            815                 820                 825

Thr Arg Asp Ser Leu Phe Phe Cys Leu Lys Phe Cys Thr Ala Ala
            830                 835                 840

Ile Ser Tyr Ser Leu Cys Lys Phe Ser Ser Gln Ser Arg Asp Thr
            845                 850                 855

Leu Cys Ser Cys Leu Ser Pro Gly Leu Ile Lys Lys Phe Gln Phe
            860                 865                 870

Leu Met Phe Arg Leu Phe Ser Glu Ala Arg Gln Pro Leu Ser Glu
            875                 880                 885

Glu Asp Val Ala Ser Leu Ser Trp Arg Pro Leu His Leu Pro Ser
            890                 895                 900

Ala Asp Trp Gln Arg Ala Ala Leu Ser Leu Trp Thr His Arg Thr
            905                 910                 915
```

-continued

Phe Arg Glu Val Leu Lys Glu Glu Asp Val His Leu Thr Tyr Gln
            920                 925                 930

Asp Trp Leu His Leu Glu Leu Glu Ile Gln Pro Glu Ala Asp Ala
            935                 940                 945

Leu Ser Asp Thr Glu Arg Gln Asp Phe His Gln Trp Ala Ile His
            950                 955                 960

Glu His Phe Leu Pro Glu Ser Ser Ala Ser Gly Gly Cys Asp Gly
            965                 970                 975

Asp Leu Gln Ala Ala Cys Thr Ile Leu Val Asn Ala Leu Met Asp
            980                 985                 990

Phe His Gln Ser Ser Arg Ser Tyr Asp His Ser Glu Asn Ser Asp
            995                 1000                1005

Leu Val Phe Gly Gly Arg Thr Gly Asn Glu Asp Ile Ile Ser Arg
            1010                1015                1020

Leu Gln Glu Met Val Ala Asp Leu Glu Leu Gln Gln Asp Leu Ile
            1025                1030                1035

Val Pro Leu Gly His Thr Pro Ser Gln Glu His Phe Leu Phe Glu
            1040                1045                1050

Ile Phe Arg Arg Arg Leu Gln Ala Leu Thr Ser Gly Trp Ser Val
            1055                1060                1065

Ala Ala Ser Leu Gln Arg Gln Arg Glu Leu Leu Met Tyr Lys Arg
            1070                1075                1080

Ile Leu Leu Arg Leu Pro Ser Ser Val Leu Cys Gly Ser Ser Phe
            1085                1090                1095

Gln Ala Glu Gln Pro Ile Thr Ala Arg Cys Glu Gln Phe Phe His
            1100                1105                1110

Leu Val Asn Ser Glu Met Arg Asn Phe Cys Ser His Gly Gly Ala
            1115                1120                1125

Leu Thr Gln Asp Ile Thr Ala His Phe Phe Arg Gly Leu Leu Asn
            1130                1135                1140

Ala Cys Leu Arg Ser Arg Asp Pro Ser Leu Met Val Asp Phe Ile
            1145                1150                1155

Leu Ala Lys Cys Gln Thr Lys Cys Pro Leu Ile Leu Thr Ser Ala
            1160                1165                1170

Leu Val Trp Trp Pro Ser Leu Glu Pro Val Leu Leu Cys Arg Trp
            1175                1180                1185

Arg Arg His Cys Gln Ser Pro Leu Pro Arg Glu Leu Gln Lys Leu
            1190                1195                1200

Gln Glu Gly Arg Gln Phe Ala Ser Asp Phe Leu Ser Pro Glu Ala
            1205                1210                1215

Ala Ser Pro Ala Pro Asn Pro Asp Trp Leu Ser Ala Ala Ala Leu
            1220                1225                1230

His Phe Ala Ile Gln Gln Val Arg Glu Glu Asn Ile Arg Lys Gln
            1235                1240                1245

Leu Lys Lys Leu Asp Cys Glu Arg Glu Glu Leu Leu Val Phe Leu
            1250                1255                1260

Phe Phe Phe Ser Leu Met Gly Leu Leu Ser Ser His Leu Thr Ser
            1265                1270                1275

Asn Ser Thr Thr Asp Leu Pro Lys Ala Phe His Val Cys Ala Ala
            1280                1285                1290

Ile Leu Glu Cys Leu Glu Lys Arg Lys Ile Ser Trp Leu Ala Leu
            1295                1300                1305

Phe Gln Leu Thr Glu Ser Asp Leu Arg Leu Gly Arg Leu Leu Leu

```
                1310                1315               1320
Arg Val Ala Pro Asp Gln His Thr Arg Leu Leu Pro Phe Ala Phe
            1325                1330                1335
Tyr Ser Leu Leu Ser Tyr Phe His Glu Asp Ala Ala Ile Arg Glu
            1340                1345                1350
Glu Ala Phe Leu His Val Ala Val Asp Met Tyr Leu Lys Leu Val
            1355                1360                1365
Gln Leu Phe Val Ala Gly Asp Thr Ser Thr Val Ser Pro Pro Ala
            1370                1375                1380
Gly Arg Ser Leu Glu Leu Lys Gly Gln Gly Asn Pro Val Glu Leu
            1385                1390                1395
Ile Thr Lys Ala Arg Leu Phe Leu Leu Gln Leu Ile Pro Arg Cys
            1400                1405                1410
Pro Lys Lys Ser Phe Ser His Val Ala Glu Leu Leu Ala Asp Arg
            1415                1420                1425
Gly Asp Cys Asp Pro Glu Val Ser Ala Ala Leu Gln Ser Arg Gln
            1430                1435                1440
Gln Ala Ala Pro Asp Ala Asp Leu Ser Gln Glu Pro His Leu Phe
            1445                1450                1455

(2) INFORMATION FOR SEQ ID NO:3:

(i) SEQUENCE CHARACTERISTICS:
        (A) LENGTH: 45
        (B) TYPE: nucleic acid
        (C) STRANDEDNESS: single
        (D) TOPOLOGY: linear (xi) SEQUENCE DESCRIPTION: SEQ ID NO:3:

GCGTAATACG ACTCACTATA GGGATGGTTG CCTCTAGCGT GGGAC                    45

(2) INFORMATION FOR SEQ ID NO:4:

(i) SEQUENCE CHARACTERISTICS:
        (A) LENGTH: 23
        (B) TYPE: nucleic acid
        (C) STRANDEDNESS: single
        (D) TOPOLOGY: linear (xi) SEQUENCE DESCRIPTION: SEQ ID NO:4:

TGATATCTCA ACGCTGCTGT CAT                                            23

(2) INFORMATION FOR SEQ ID NO:5:

(i) SEQUENCE CHARACTERISTICS:
        (A) LENGTH: 59
        (B) TYPE: nucleic acid
        (C) STRANDEDNESS: single
        (D) TOPOLOGY: linear (xi) SEQUENCE DESCRIPTION: SEQ ID NO:5:

CGCTAATACG ACTCACTATA GGAACAGACC ACCATGGCCA TCATGGTGTT TGAGCATAC     59

(2) INFORMATION FOR SEQ ID NO:6:

(i) SEQUENCE CHARACTERISTICS:
        (A) LENGTH: 26
        (B) TYPE: nucleic acid
        (C) STRANDEDNESS: single
        (D) TOPOLOGY: linear (xi) SEQUENCE DESCRIPTION: SEQ ID NO:6:

CCGAGGACTC AGGGAGAAAG TGCTCA                                         26
```

(2) INFORMATION FOR SEQ ID NO:7:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:7:

TGTTCTCCCG TCTTTCCTTC    20

(2) INFORMATION FOR SEQ ID NO:8:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO:8:

GTGAGCAGAG GGTGTGTC    18

(2) INFORMATION FOR SEQ ID NO:9:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:9:

GTTCGGAGTG TTCAGTGGAC    20

(2) INFORMATION FOR SEQ ID NO:10:

(i) SEQUENCE CHARACTERISTICS:
        (A) LENGTH: 19
        (B) TYPE: nucleic acid
        (C) STRANDEDNESS: single
        (D) TOPOLOGY: linear (xi) SEQUENCE DESCRIPTION: SEQ ID NO:10:

GGGTGGGGTG GAGAATGTG    19

(2) INFORMATION FOR SEQ ID NO:11:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:11:

GGCCCTGGTC TTCCTGTTTA    20

(2) INFORMATION FOR SEQ ID NO:12:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:12:

CCTCAGCAGA GTTGGGTTCT    20

(2) INFORMATION FOR SEQ ID NO:13:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:13:

GACTCCCGTG TGGCGTTTAT                                                          20

(2) INFORMATION FOR SEQ ID NO:14:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:14:

CAGCACATGT GGGGCACTCA                                                          20

(2) INFORMATION FOR SEQ ID NO:15:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO:15:

AGCCGCCGCC GGGGCTGTAG GCGC                                        24

(2) INFORMATION FOR SEQ ID NO:16:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO:16:

TAAGGAAATA GCTTTCTGAG GTTT                                        24

(2) INFORMATION FOR SEQ ID NO:17:

(i) SEQUENCE CHARACTERISTICS:
        (A) LENGTH: 27
        (B) TYPE: nucleic acid
        (C) STRANDEDNESS: single
        (D) TOPOLOGY: linear (xi) SEQUENCE DESCRIPTION: SEQ ID NO:17:

ATGTCCGACT CGTGGGTCCC GAACTCC                                 27

(2) INFORMATION FOR SEQ ID NO:18:

(i) SEQUENCE CHARACTERISTICS:
        (A) LENGTH: 27
        (B) TYPE: nucleic acid
        (C) STRANDEDNESS: single
        (D) TOPOLOGY: linear (xi) SEQUENCE DESCRIPTION: SEQ ID NO:18:

TCAGAAGAGA TGAGGCTCCT GGGACAG                                 27